(12) United States Patent
Rice, III et al.

(10) Patent No.: US 7,455,969 B2
(45) Date of Patent: Nov. 25, 2008

(54) HIGHLY PERMISSIVE CELL LINES FOR HEPATITIS C VIRUS RNA REPLICATION

(75) Inventors: Charles M. Rice, III, New York, NY (US); Keril J. Blight, St. Louis, MO (US)

(73) Assignee: Washington University, St. Louis, MO (US)

( * ) Notice: Subject to any disclaimer, the term of this patent is extended or adjusted under 35 U.S.C. 154(b) by 234 days.

(21) Appl. No.: 10/534,571

(22) PCT Filed: Nov. 13, 2003

(86) PCT No.: PCT/US03/36634

§ 371 (c)(1),
(2), (4) Date: Oct. 11, 2005

(87) PCT Pub. No.: WO2004/044182

PCT Pub. Date: May 27, 2004

(65) Prior Publication Data

US 2006/0099595 A1    May 11, 2006

Related U.S. Application Data

(60) Provisional application No. 60/426,256, filed on Nov. 13, 2002.

(51) Int. Cl.
| | | |
|---|---|---|
| C12Q 1/68 | (2006.01) | |
| C12Q 1/70 | (2006.01) | |
| C12N 15/00 | (2006.01) | |
| C12N 5/00 | (2006.01) | |
| C12N 5/08 | (2006.01) | |
| C07H 21/00 | (2006.01) | |

(52) U.S. Cl. .................. 435/6; 435/5; 435/440; 435/455; 435/325; 435/370; 536/23.72
(58) Field of Classification Search .............. None
See application file for complete search history.

(56) References Cited

U.S. PATENT DOCUMENTS 6,127,116 A    10/2000 Rice 6,630,343 B1    10/2003 Bartenschlager

FOREIGN PATENT DOCUMENTS

| EP | 1 267 167 A1 | 12/2002 | |
|---|---|---|---|
| WO | WO 01/89364 | 11/2001 | |
| WO | WO 02/059321 | * 8/2002 | |

OTHER PUBLICATIONS

Lanford et al., "Advances in Model Systems for Hepatitis C Virus Research," Virology, vol. 293 No. 1, pp. 1-9 (Feb. 2002).*
Lindenbach et al., "Cell culture-grown hepatitis C virus is infectious in vivo and can be recultured in vitro," Proceedings of the National Academy of Sciences, USA, vol. 103 No. 10, pp. 3805-3809 (Mar. 2006).*
Sheehy et al., "In vitro replication models for the hepatitis C virus," Journal of Viral hepatitis, Col No. 1, pp. 2-10 (Jan. 2007).*
Keril Blight, Highly Permissive Cell Line for Subgenomic and Genomic Hepatitis C Virus RNA Replication, Journal of Virology, Dec. 2002, vol. 76 No. 24, pp. 13001-13014.
Raymond T. Chung, Hepatitis C Virus Replication is Directly Inhibited by IFN-alpha in a Full-Length Binary Expression System, Proceedings of the National Academy of Sciences, Aug. 2001, vol. 98 No. 17, pp. 9847-9852, USA.
Ralf Bartenschlager, Replication of the Hepatitis C Virus in Cell Culture, Antiviral Research, Oct. 2003, vol. 60 No. 2, pp. 91-102, Elsevier.
Blight et al., "Efficient initiation of HCV RNA replication in cell culture", *Science* 290:1972-4 (2002).
Krieger et al., "Enhancement of hepatitis C virus RNA replication by cell culture-adaptive mutations", *J Virol.* 75:4614-24 (2001).
Murray et al., "Persistent replication of hepatitis C virus replicons expressing the beta-lactamase reporter in subpopulations of highly permissive Huh7 cells", *J Virol.* 77:2928-35 (2003).

* cited by examiner

*Primary Examiner*—Zachariah Lucas
(74) *Attorney, Agent, or Firm*—Thompson Coburn LLP; Charles P. Romano

(57) ABSTRACT

This invention relates generally to cells and cell lines that are permissive for hepatitis C virus (HCV) replication, and methods and materials for making and using them. The subject cell line referred to as Huh-7.5 has the A.T.C.C. designation number PTA-8561, having been deposited on Aug. 1, 2007.

12 Claims, 9 Drawing Sheets

B

S2204I

Q1112R+S2204I

E1202G+T1280I+S2204I pol⁻ ial stage application of PCT Patent Application No. PCT/U.S.2003/36634, filed Nov. 13, 2003, which claims priority to U.S. Provisional Application No. 60/426,256, filed Nov. 13, 2002.

HIGHLY PERMISSIVE CELL LINES FOR HEPATITIS C VIRUS RNA REPLICATION

CROSS-REFERENCE TO RELATED APPLICATIONS

This application is the national stage application of PCT Patent Application No. PCT/U.S.2003/36634, filed Nov. 13, 2003, which claims priority to U.S. Provisional Application No. 60/426,256, filed Nov. 13, 2002.

STATEMENT REGARDING FEDERALLY SPONSORED RESEARCH OR DEVELOPMENT

This invention was made with U.S. Government support under grant numbers CA57973 and AI40034. The U.S. Government may have certain rights in this invention.

BACKGROUND

1. Field of the Invention

This invention relates generally to cells that are permissive for hepatitis C virus (HCV) replication, and methods and materials for making and using them.

2. Related Art

Adaptive mutations in the HCV non-structural proteins that increase RNA replication, and the frequency of Huh-7 cells supporting detectable levels of replication, have been identified previously. (Blight, K. J. et al, Science 290:1972-1974, 2000; Guo, J. T. et al., J. Virol. 75:8516-8523, 2001; Kreiger, N. et al., J. Virol. 75:4614-4624, 2001; Lohmann, V. et al., J. Virol. 75:1437-1449, 2001). In particular, replacement of the Serine residue with Isoleucine at position 2204 in NS5A permits HCV replication in ~10% of transfected Huh-7 cells (a 20,000-fold improvement over non-mutated HCV) and increases replication to a level sufficient for the detection of HCV RNA early after transfection. (Blight et al., 2000). The low frequency of Huh-7 cells supporting HCV replication suggests that the cellular environment may be a major determinant of HCV replication efficiency.

DESCRIPTION

Figure 1:
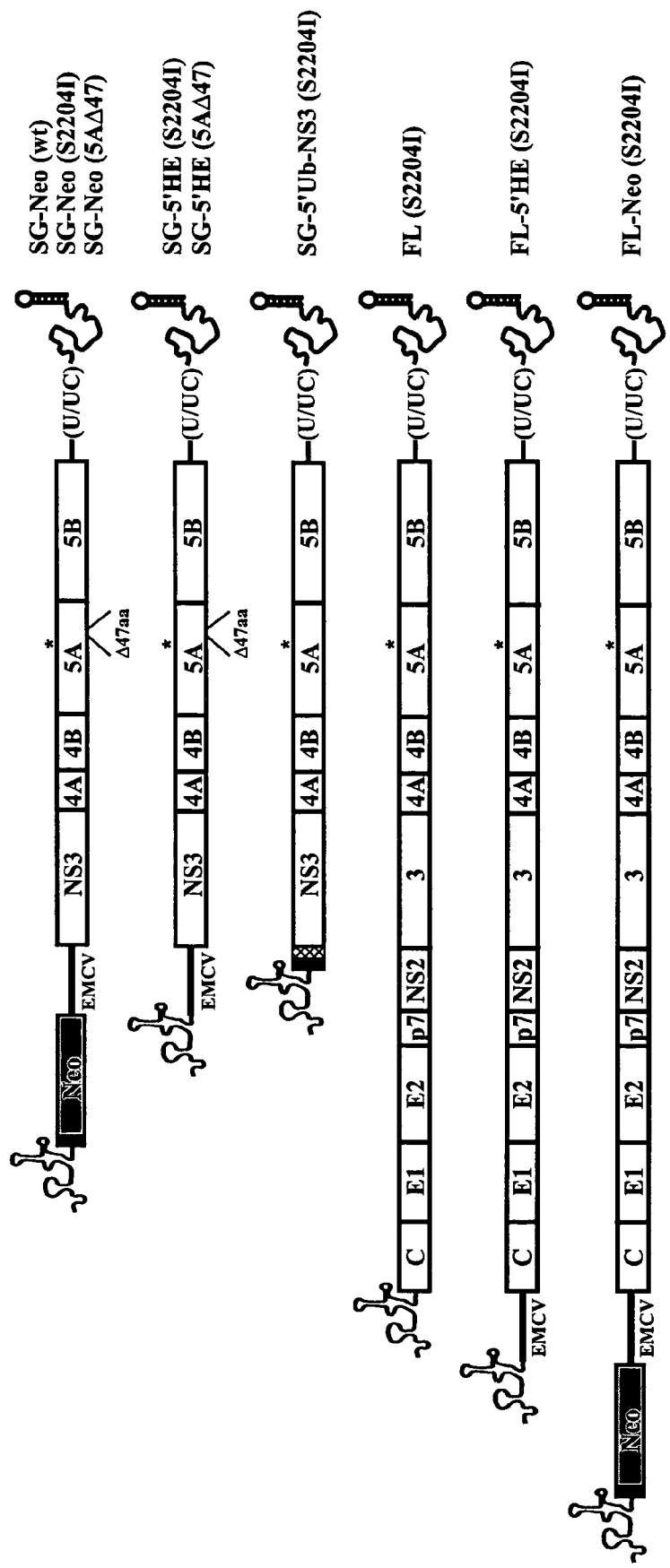
FIG. 1 shows schematic representations of various HCV RNAs.

As used herein the term "permissive" for HCV replication, in reference to a particular cell or cell line, means that the particular cell or cell line supports HCV replication at a frequency that is greater than that of the cell or cell line from which it was derived. For example, in certain embodiments described herein, Huh-7 sublines support a higher frequency of HCV replication than the Huh-7 cell line from which they were derived. Thus, the sublines are said to be permissive for HCV replication. In some embodiments, the cell or cell line supports replication of HCV at a frequency of between about 10% to about 30%. In other embodiments, the cell or cell line supports replication of HCV at a frequency of between about 10% and about 75%.

The term "cured" refers to cells substantially free of self-replicating HCV RNA. Example 1 provides a description of one means for curing cells, within the meaning of that term as used herein.

The term "transfection" refers to the infection of a cell with a polynucleotide. The polynucleotide may be either DNA or RNA. Methods of transfecting a cell are known in the art, any of which may be used.

Frequency is ascertained by determining the percent of cells having replicating HCV RNA. One easy way to measure frequency is to determine the percentage of cells that exhibit a characteristic conferred by the HCV RNA, and any method known in the art for accomplishing this is suitable. The examples herein describe such a method utilizing HCV RNA comprising a neo gene and G418 selection.

Unless otherwise noted, conventional techniques of cell culture, molecular biology, microbiology, recombinant DNA and immunology are employed, all of which are within the skill of the art and are described in the literature.

In order to obtain cell lines permissive for HCV replication, clonal and population Huh-7 cell lines supporting adapted and non-adapted subgenomic or full-length RNA replication were cured of HCV RNA by treatment with interferon (IN). Since HCV replication can be readily blocked by IFN, prolonged treatment with IFN cures cells of HCV RNA. A higher percentage of cured cells were able to support HCV replication and facilitated the detection of both subgenomic and full-length replication by multiple assays. Thus, one embodiment described herein comprises a method of making cells and cell lines that are permissive for HCV replication. Such a method comprises curing HCV infected cells. The cured cells may then be assayed to determine the frequency at which cells support HCV replication.

The cells may be any vertebrate cells that are capable of supporting adapted or non-adapted HCV RNA replication. The methods described herein for making cells and cell lines are believed to be applicable to any cell type that is capable of supporting adapted or non-adapted HCV RNA replication. Such cells may include, for example, hepatocytes, T-cells, B-cells, or foreskin fibroblasts, and may be mammalian or more specifically human cells. A particularly useful cell type is hepatocyte cells. For example, Huh-7 cells have been shown to support HCV RNA replication.

It is demonstrated herein that Huh-7 sublines that have been cured are permissive for HCV RNA replication. For the replicon containing the highly adaptive NS5A S2204I mutation, at least 30% of the Huh-7.5 cells can be transduced to G418 resistance. A comparable fraction was positive for the NS3 antigen by FACS. Similarly, for the SG replicons lacking neo (FIG. 1), at least 50% initiation efficiency was achieved. Data from more sensitive FACS analysis (data not shown) indicates that >75% of the cells that survive the transfection procedure harbor replicating HCV RNAs. These permissive cells were obtained by curing replicon-containing cell clones with IFN.

Other embodiments comprise methods of making cells and cell lines that are permissive for HCV replication. Such methods comprise curing infected cells, and subsequently assaying sublines to determine the frequency with which a particular subline supports HCV replication. Sublines that are particularly permissive may then be identified. The infected cells may be cured by any means. For example, treatment with interferon-α is an effective means of curing cells of HCV infection, although any effective means of curing may be utilized within the scope of this invention.

The most highly permissive sublines (Huh-7.5 and Huh-7.8) were obtained from G418-selected clones that harbored replicons without adaptive changes in the NS3-5B region (at the population sequence level). These cells may represent a subpopulation of the original Huh-7 parental line that are permissive for replication of unmodified replicons as well as more permissive for replicons with adaptive mutations. Curing of other replicon-containing cell lines did not always yield a cell population that was more permissive for the replicons tested. For instance, curing the Huh-7 population containing the SG-Neo (S2204I) replicon, yielded a cell substrate that was unchanged in its ability to support SG-Neo (S2204I), but less efficient (23-fold) for initiation of SG-Neo (5AΔ47) (FIG. 2).

Cultures of Human Hepatocyte Cell Line Huh-7.5 were deposited in the permanent collection of the American Type Culture Collection (ATCC), 10801 University Blvd., Manassas, Va. 20110, U.S.A. on Aug. 1, 2007 under the terms of the Budapest Treaty, and accorded the accession number PTA-8561. The subject culture deposit will be stored and made available to the public in accordance with the provisions of the Budapest Treaty, i.e., they will be stored for a period of at least 30 (thirty) years after the date of deposit, or five years after the most recent request for a sample, whichever is longer. The depositor acknowledges and accepts the duty to replace the deposits with a living culture of the same should the deposited culture die or be destroyed. All restrictions on the availability to the public of the subject culture deposit will be irrevocably removed upon the granting of a patent disclosing them.

The ability to study HCV replication directly after transfection, without the need for G418 selection, allowed for examination of replication of subgenomic replicons lacking neo as well as full-length HCV genome RNAs. Initial attempts to create a monocistronic replicon by fusing cellular ubiquitin in-frame between the first 12 amino acids of core and NS3 {SG-5'Ub-NS3 (S2204I); FIG. 1} were unsuccessful. A bicistronic derivative with ubiquitin fused to NS3-5B was viable, suggesting that the failure of SG-5'Ub-NS3 (S2204I) to replicate was not due to a defect in processing at the ubiquitin/NS3 junction (data not shown). Rather, the fusion of the ubiquitin-coding sequence near the HCV 5' NTR may have interfered with translation due to the formation of deleterious RNA secondary structures or RNA replication, by disrupting RNA elements that lie in the HCV 5' NTR or its complement. Fusion of the HCV 5' NTR to the EMCV IRES yielded a subgenomic replicon that replicated better than SG-Neo (S2204I) (FIG. 3). Why deletion of the first cistron (sequences encoding C-Neo fusion) from the bicistronic SG-Neo (S2204I) stimulated replication is unknown, but may result from enhanced translation of the replicase due to abrogated binding of the 40S ribosomal subunit to the usual HCV translation initiation site and diminished competition between the EMCV and HCV IRES elements (J. Marcotrigiano and C. M. Rice, unpublished results).

A similar picture was observed for replication of the full-length constructs containing the NS5A S2204I adaptive change (FIG. 4). In Huh-7.5 cells, the bicistronic construct containing the C-Neo cistron {FL-Neo (S2204I); FIG. 1} initiated replication less efficiently than the RNA with the HCV 5' NTR fused to the EMCV IRES {FL-5'HE (S2204I); FIG. 1}. The FL construct with the unmodified HCV genome (except for the S2204I substitution in NS5A) was better at initiating replication than RNA where translation was mediated by the EMCV IRES (FIG. 4), demonstrating that EMCV IRES-driven translation is not required for HCV replication in Huh-7.5 cells, thus allowing the study of unmodified HCV genomic RNAs. This latter point could certainly impact the ability of HCV RNAs to be packaged into infectious particles. However, in our hands (K. J. Blight and C. M. Rice, unpublished results) and in a recent report (Pietschmann, T. et al., J. Virol. 76:4008-4021, 2002) selective packaging of these unmodified FL RNAs was not observed in Huh-7 cells. Full-length HCV RNAs were less efficient at establishing replication than the corresponding adapted subgenomic replicons, suggesting that addition of the structural-NS2 coding region inhibits HCV replication initiation. Whether this is due to the encoded proteins or RNA elements that lie in this region (or both) (31) is currently unclear. We have observed that the levels of HCV replication (as measured by HCV protein and RNA levels) of S2204I-containing FL and FL-Neo RNAs, but not subgenomic replicons, is dependent upon the cell cycle which might compromise the ability of the full-length RNAs to initiate replication in an unsynchronized transfected cell population (Balfe et al., submitted).

In an attempt to further enhance HCV replication in cell culture, the effect of other amino acid substitutions at position 2204 in NS5A was examined. Efficient subgenomic RNA replication was observed for Ile and Val and to a much lesser extent, Ala at position 2204 (FIG. 5). Val or Ile are small, β-branched, non-polar residues, whereas Ala has similar properties, but is not β-branched. In contrast, polar residues such as Tyr, Glu, Thr, Ser or Asp at position 2204 severely impaired HCV replication (FIG. 5), suggesting that replication favors non-polar residues at this locus. It is interesting to note that Ser is found naturally at position 2204 for this genotype 1b isolate (Lohmann, V. et al., Science 285:110-113, 1999) and is conserved between other HCV genotypes (Tanji, Y. et al., J. Virol. 69:3980-3986, 1995), suggesting that this residue may be important for HCV replication and/or pathogenesis in vivo.

Combining NS5A adaptive mutations resulted in replicons that were either impaired (A2199T+S2204I) or unable to replicate (S2197P+A2199T+S2204I) in Huh-7.5 cells (FIG. 6). Incompatability of adaptive mutations elsewhere in the HCV NS coding region has been previously described (Lohmann, V. et al., J. Virol. 75:1437-1449). For example, combining an adaptive mutation in NSSB (R2884G) with either NS4B (P1936S) or NS5A (E2163G) drastically reduced the efficiency of G418-resistant colony formation. On the other hand, combining certain NS3 and NS5A adaptive mutations can increase replication efficiency (Krieger, N. et al., J. Virol. 75:4614-4624, 2001). However, despite the observation that mutations E1202G and T1280I in NS3 act synergistically with S2197P in NS5A to increase the replication efficiency (Krieger et al., 2001, and K. J. Blight and C. M. Rice, unpublished results), engineering these NS3 changes into SG-5'HE (S2204I) did not enhance replication in our system (FIG. 7). These results again underscore the empirical nature of optimizing adaptive mutations with different Huh-7 cellular environments.

The phosphorylation of NS5A is conserved among divergent HCV genotypes (Reed, K. E. et al, J. Virol. 71:7187-7197, 1997) suggesting that it plays an important role in the virus life cycle. We previously showed that NS5A hyperphosphorylation is not essential for HCV replication (Blight, K. J.

et al., Science 290:1972-1974, 2000). Following the recent identification of S2194 as a major phosphate acceptor site for subtype 1b (Katze, M. G. et al, Virology 278:501-513), Ala or Asp was substituted at this position and the effect on HCV replication was examined in the context of the S2204I adaptive mutation. Given the incompatibilities observed when combining NS5A mutations, the absolute replication efficiencies of the different mutants could not be evaluated, however replicating RNAs were recovered that harbored these substitutions at the 2194 locus. These results show that phosphorylation at S2194 is not an absolute requirement for replication of this subtype 1b isolate.

Various embodiments of the invention are described in the following examples. These examples are to be considered exemplary only, and are not intended to be limiting.

EXAMPLES

Example 1

Cell Culture and Interferon Treatment

Huh-7 cell monolayers were propagated in Dulbecco's modified minimal essential medium (DMEM) supplemented with 10% heat-inactivated fetal bovine serum (FBS) and 0.1 mM non-essential amino acids (DMEM-10% FBS). For cells supporting subgenomic replicons, 750 µg/ml G418 (Geneticin; Gibco-BRL) was added to the culture medium. Replicon-containing Huh-7 cells were cured of HCV RNA by initially passaging cells twice in the absence of G418. On the third passage cells were cultured with 100 IU/ml of human leukocyte-derived IFN (Sigma-Aldrich). After 3-4 days, confluent monolayers were trypsinized, plated and cultured for 24 h before the addition of IFN. Cells were passaged a total of four times in the presence of IFN and prior to the fourth passage cells were grown for 3 days without IFN. Cured cell lines were expanded and cryopreserved at early passage levels. Further experiments were conducted using cells that been passaged less that 20-30 times from these cryopreserved seed lots.

Example 2

Plasmid Construction

Standard recombinant DNA technology was used to construct and purify all plasmids. Primed DNA synthesis was performed with KlenTaqLA DNA polymerase (kindly provided by Wayne Barnes, Washington University, St. Louis), and regions amplified by PCR were confirmed by automated nucleotide sequencing. Plasmid DNAs for in vitro transcription were prepared from large-scale bacterial cultures and purified by centrifugation in CsCl gradients.

All nucleotides (nt) and amino acid numbers refer to the location within the genotype 1b Con1 full-length HCV genome (Genbank Accession no. AJ238799; SEQ ID NO:27) commencing with the core-coding region. This sequence was assembled from chemically synthesized DNA oligonucleotides in a step-wise PCR assay essentially as described previously (5). Briefly, 10-12 gel-purified oligonucleotides (60-80 nt in length) with unique complementary overlaps of 16 nt were used to synthesize cDNAs spanning 600-750 bases. The final PCR products were purified, digested with appropriate restriction enzymes, and ligated into the similarly cleaved pGEM3Zf(+) plasmid vector (Promega). Multiple recombinant clones were sequenced, correct clones identified and overlapping cDNA fragments assembled into the contiguous genomic sequence: 5'NTR-C-E1-E2-p7-NS2-3-4A-4B-5A-5B-3'NTR (pHCVBMFL). The selectable replicon, pHCVrep1bBartMan/AvaII {SG-Neo (wt); FIG. 1 }and the derivatives, pHCVrep1b/BBVII {SG-Neo (S2204I)}and pHCVrep1b/BBI {SG-Neo (5AΔ47)}, containing the NS5A adaptive mutations, S2204I and an in-frame deletion of 47 amino acids (Δ47aa) between nt 6960 and 7102, respectively, have been described (5) (FIG. 1). The plasmid pHCVBMFL/S2204I {FL (S2204I); FIG. 1 }contains the full-length genome with the NS5A adaptive change S2204I. For the genomic and subgenomic constructs, NS5B polymerase defective derivatives were generated carrying a triple amino acid substitution, changing the Gly-Asp-Asp (GDD) motif in the active site to Ala-Ala-Gly (AAG) (5), and throughout this report are referred to as pol-.

The plasmid pC-Ubi-NS3/HCVrepBBVII {SG-5'Ub-NS3 (S2204I); FIG. 1} containing ubiquitin instead of the neo gene and EMCV IRES was constructed as follows. An AscI-SacI digested PCR fragment amplified from pHCVrep12/Neo (Blight et al., unpublished results) with primers 1289 and 1290 (Table 1) and the SacI-BsrGI portion of a second PCR product generated using the primer pair 1291/1292 (Table 1) with pHCVrep1b/BBVII were ligated between the XbaI and BsrGI sites of HCVrep1b/BBVII together with the XbaI-AscI fragment from HCVrep1b/BBVII. To delete the neo gene from pHCVrep1b/BBVII, synthetic overlapping oligonucleotides 1287 and 1288 (Table 1) were hybridized and extended to create the junction between the 5' NTR and the EMCV IRES. This product was digested with ApaLI and AclI, and inserted, together with XbaI-ApaLI and AclI-EcoRI fragments from pHCVrep1b/BBVII, into XbaI-EcoRI digested pHCVrep1b/BBVII. This construct was named p5'NTR-EMCV/HCVrepBBVII {SG-5'HE (S2204I); FIG. 1}. To replace S2204I with NS5AΔ47, the EcoRI-XhoI fragment from pHCVrep1b/BBI was ligated into similarly cleaved p5'NTR-EMCV/HCVrepBBVII, generating p5'NTR-EMCV/HCVrepBBI {SG-5'HE (5AΔ47); FIG. 1}.

The plasmid p5'NTR-EMCV/HCVFLBM(S2204I) {FL-5'HE (S2204I); FIG. 1} was created by ligating the XbaI-HindIII fragment from p5'NTR-EMCV/HCVrepBBVII, the HindIII-AatII fragment of a PCR product amplified from p5'NTR-EMCV/HCVrepBBVII using primers 1293 and 1294 and the AatII-NotI fragment from pHCVBMFL/S2204I into pHCVBMFL/S2204I previously digested with XbaI and NotI. The selectable bicistronic full-length HCV clone pHCVBMFL(S2204I)/Neo {FL-Neo (S2204I); FIG. 1} was assembled by ligating the XbaI-HindIII fragment from pHCVrep1b/BBVII and the HindIII-EcoRI fragment from p5'NTR-EMCV/HCVBMFL(S2204I) between the XbaI and EcoRI sites of pHCVrep1b/BBVII.

To obtain plasmids with mutations at position 2204, and to introduce single A2199T or double S2197P/A2199T mutations into p5'NTR-EMCV/HCVrepBBVII, PCRs were first performed using p5'NTR-EMCV/HCVrepBBVII as a template with the reverse primer 1030 and one of the following mutant forward primers: 1319 (S2204V), 1320 (S2204A), 1322 (S2204Y), 1324 (S2204E), 1325 (S2204T), 1184 (S2204D), 1326 (A2199T+S2204I) and 1327 (S2197P+A2199T+S2204I) (Table 1). PCR-amplified products were digested with BlpI and XhoI and cloned into these sites in p5'NTR-EMCV/HCVrepBBVII. S2204 was engineered by insertion of the EcoRI-XhoI fragment from pHCVrep1bBartMan/AvaII into similarly cleaved p5'NTR-EMCV/HCVrepBBVII.

To engineer the mutation, Q1112R, into p5'NTR-EMCV/HCVrepBBVII in order to create p5'NTR-EMCV/HCVrep-CloneA (Q1112R+S2204I), nt 3640-3991 of NS3 were PCR amplified from p5'NTR-EMCV/HCVrepBBVII using mutant primer 1358 and oligonucleotide 885 (Table 1). The resulting product was digested with BsrGI and EagI and combined in a ligation reaction mixture with the EagI-EcoRI and BsrGI-EcoRI fragments from p5'NTR-EMCV/ HCVrepBBVII. The double mutation (E1202G+T1280I) in NS3 was created via a multistep cloning procedure. First, a PCR fragment amplified from p5'NTR-EMCV/HCVrepB-BVII with forward primer 1359 and reverse primer 1356 (Table 1) was digested with ApaLI and XbaI and cloned into EcoRI-XbaI digested pGEM3Zf(+) together with the EcoRI-ApaLI fragment from pGEM3Zf(+)/HCV1bnt1796-2524, containing nt 3420-4124 in NS3 (K. J. Blight and C. M. Rice, unpublished results), generating the intermediate plasmid pGEM3Zf(+)/HCV1bnt1796-2524NS3*. Second, in a four part cloning strategy, the BsrGI-BsaAI fragment, excised from pGEM3Zf(+)/HCV1bnt1796-2524NS3*, was inserted, together with fragments BsaAI-BssHII and BssHII-EcoRI from p5'NTR-EMCV/HCVrepBBVII, into p5'NTR-EMCV/ HCVrepBBVII cleaved with BsrGI and EcoRI. The resultant plasmid was named p5'NTR-EMCV/HCVrepBBVII+NS3* (E1202G+T1280I+S2204I).

The mutations S2194A and S2194D were introduced by using primer pairs 5'Ala/1030 and 5'Asp/1030 (Table 1), respectively to PCR amplify nt 6897-7186 in NS5A from pHCVrep1b/BBVIII. These mutations were incorporated into pHCVrep1b/BBVII by replacing the BlpI-XhoI portion with the corresponding BlpI-XhoI digested PCR product.

Example 3

RNA Transcription

Plasmid DNAs containing full-length and subgenomic HCV sequences were linearized with ScaI and a poliovirus subgenomic replicon digested with BamHI. The linearized DNAs were phenol:chloroform (1:1) extracted, and precipitated with ethanol. Pelleted DNAs were washed in 80% ethanol and resuspended in 10 mM Tris-HCl (pH 8.0)/1 mM EDTA (pH 8.0). RNA transcripts were synthesized at 37° C. for 90 min in a 100 µl reaction mixture containing 40 mM Tris-HCl (pH 7.9), 10 mM NaCl, 12 mM $MgCl_2$, 2 mM spermidine, 10 mM dithiothreitol (DTT), 3 mM of each nucleoside triphosphate, 0.025 U of inorganic pyrophosphatase (Roche Applied Science), 100 U of RNasin (Promega), 100 U of T7 RNA polymerase (Epicentre Technologies), and 2 µg of linearized DNA. RNA was extracted with phenol-chloroform (1:1), ethanol precipitated, and the pellet washed in 80% ethanol before resuspension in $ddH_2O$. DNA template was removed by three serial DNase digestions for 20 min at 37° C. in 33 mM Tris-HCl (pH 7.8), 66 mM KCl, 10 mM $MgCl_2$ and 5 mM DTT containing 10 U of DNase I (Roche Applied Science). DNase-digested RNAs were extracted with phenol:chloroform (1:1), ethanol precipitated and the RNA pellet resuspended in $ddH_2O$ after washing in 80% ethanol. The RNA concentration was determined by measurement of the optical density at 260 nm and the integrity and concentration confirmed by 1% agarose gel electrophoresis and ethidium bromide staining.

Example 4

Transfection of Cultured Cells

In vitro-transcribed RNA was transfected into Huh-7 and IFN-cured cells by electroporation. Briefly, subconfluent Huh-7 cells were detached by trypsin treatment, collected by centrifugation (500×g, 5 min), washed three times in ice-cold RNase-free phosphate-buffered saline (PBS) and resuspended at $1.25×10^7$ cells/ml in PBS. RNA transcripts (1 µg) were mixed with 0.4 ml of washed Huh-7 cells in a 2-mm gap cuvette (BTX) and immediately pulsed (0.92 kV, 99 µsec pulse-length, 5 pulses) using a BTX ElectroSquarePorator. Pulsed cells were left to recover for 10 min at room temperature (rt) and then diluted into 10 ml DMEM-10% FBS. Cells were plated in: (i) 35-mm diameter wells for quantifying HCV RNA and for metabolic labeling experiments; (ii) eight-well chamber slides (Becton Dickinson) for immunofluorescence studies or; (iii) 100-mm diameter dishes for fluorescent activated cell sorting (FACS) analysis and G418 selection. To determine the efficiency of G418-resistant colony formation, transfected cells were plated at multiple densities (between $1×10^3$ and $2×10^5$ cells), together with cells transfected with pol RNA transcripts such that the total cell number was maintained at $2×10^5$ cells per 100-mm diameter dish. Forty-eight hours after plating, medium was replaced with DMEM-10% FBS supplemented with 1 mg/ml G418. Three weeks later, G418 resistant foci were fixed with 7% formaldehyde and stained with 1% crystal violet in 50% ethanol to facilitate colony counting. The G418 transduction efficiency was calculated based on the number of G418-selected colonies relative to the number of Huh-7 cells plated after electroporation.

Transfection efficiency was monitored for each series of RNAs by electroporating in parallel a poliovirus subgenomic replicon expressing green fluorescent protein (GFP; A. A. Kolykhalov and C. M. Rice, unpublished results). Transfected cells were observed for poliovirus replicon-induced cytopathic effect and GFP expression visualized using a fluorescent inverted microscope at 12-16 h posttransfection. After 24 h, the surviving attached cells (presumably not transfected with the poliovirus replicon) were trypsinized, mixed with trypan blue and viable cells counted to determine the percentage of cells electroporated.

Example 5

Viral RNA Analysis

Total cellular RNA was isolated using TRizol reagent (Gibco-BRL) according to the Manufacturer's protocol. One-tenth of each RNA sample was used to quantify HCV-specific RNA levels using an ABI PRISM 7700 Sequence Detector (Applied Biosystems). Real time reverse transcription (RT)-PCR amplifications were performed using the TaqMan EZ RT-PCR core reagents (Applied Biosystems) and primers specific for the HCV 5' NTR: 5'-CCTCTAGAGCCATAGTG-GTCT-3' (SEQ ID NO: 1) (sense, 50 µM), 5' CCAAATCTC-CAGGCATTGAGC-3' (SEQ ID NO: 2) (antisense, 50 µM) and FAM-CACCGGAATTGCCAGGACGACCGG (SEQ ID NO: 3) probe, 10 µM; (Applied Biosystems). RT reactions were incubated for 30 min at 60° C., followed by inactivation of the reverse transcriptase coupled with activation of Taq polymerase for 7 min at 95° C. Forty cycles of PCR were performed with cycling conditions of 15 sec at 95° C. and 1 min at 60° C. Synthetic HCV RNA standards of known concentration were included with each set of reactions and used to calculate a standard curve. The real time PCR signals were analyzed using SDS v1.6.3 software (Applied Biosystems).

Example 6

FACS Analysis

Transfected cell monolayers were removed from 100-mm diameter culture dishes by versene/EDTA treatment and a single cell suspension prepared by passing cells through a 16-gauge needle and a 74 μm pore membrane. Cells were resuspended at $2\times10^6$ per ml, an equal volume of 4% paraformaldehyde added to the cell suspensions and incubated for 20 min at rt. Fixed cells were washed twice with PBS and the resultant cell pellet resuspended at $2\times10^6$ cells per ml in 0.1% saponin/PBS. After incubation for 20 min at rt, cells were stained (1 h at rt) with HCV-specific monoclonal antibodies (mAbs; core (C750), NS3 (1B6) and NS5B (12B7); all generously provided by Darius Moradpour, University of Freiburg, Freiburg, Germany) diluted to 10 μg/ml in 3% FBS/0.1% saponin/PBS. Cells were washed three times with 0.1% saponin/PBS and bound mAb detected by incubation for 1 h at rt with anti-mouse IgG conjugated to Alexa 488 (Molecular Probes) diluted 1:1000 in 3% FBS/0.1% saponin/PBS. Stained cells were washed three times with 0.1% saponin/PBS, resuspended in FACSflow buffer (BD Biosciences) and analyzed immediately using a FACS Calibur (BD Biosciences).

Example 7

Indirect Immunofluorescence

Electroporated Huh-7.5 cells seeded in eight-well chamber slides were washed with PBS and fixed in 4% paraformaldehyde for 20 min at rt. Cells were washed twice with PBS, permeabilized by incubation with 0.1% saponin/PBS for 20 min at rt and blocked with 3% goat serum for 20 min at rt. The NS5B mAb (12B7) was diluted to 10 μg/ml in 0.1% saponin/ 3% goat serum/PBS and incubated for 1 h at rt, followed by three washes with 0.1% saponin/PBS. Bound mAb were detected by incubating for 1 h at rt with anti-mouse IgG conjugated to Alexa 488 diluted 1:1000 in 0.1% saponin/3% goat serum/PBS. Nuclei were stained for 20 min at rt with 10 μg/ml Hoechst 33342 (Sigma-Aldrich) in PBS. Unbound fluorescent conjugate was removed by three washes with 0.1% saponin/PBS, cells mounted in Vectashield (Vector Laboratories) and viewed with a fluorescent microscope (Nikon, Eclipse TE300).

Example 8

Metabolic Labeling of Proteins and Immunoprecipitation

Cell monolayers in 35-mm diameter wells were incubated for 0.5-10 h in methionine-and-cysteine-deficient MEM containing $\frac{1}{40}^{th}$ the normal concentration of methionine, 5% dialyzed FBS and Express $^{35}$S-protein labeling mix (140 μCi/ml; NEN). Labeled cells were washed once with cold PBS and harvested in 200 μl of sodium dodecyl sulfate (SDS) lysis buffer (0.1 M sodium phosphate buffer (pH 7.0), 1% SDS, 1× complete protease inhibitor cocktail (Roche Applied Science), 80 μg phenylmethylsulfonyl fluoride (PMSF) per ml) and cellular DNA sheared by repeated passage through a 27.5-gauge needle. Equal amounts of protein lysates (50 μl) were heated at 75° C. for 10 min and clarified by centrifugation prior to mixing with 200 μl of TNA (50 mM Tris-HCl (pH 7.5), 150 mM NaCl, 0.67% bovine serum albumin, 1 mM EDTA, 0.33% triton X-100, 80 μg of PMSF per ml). One-μl of HCV positive patient serum (JHF) was added, and immune complexes allowed to form by incubation overnight at 4° C. with rocking. Immune complexes were collected by adding 50 μl of prewashed Pansorbin cells (Calbiochem) and incubation for 1-2 h at 4° C. with rocking. Immunoprecipitates were collected by centrifugation and washed three times in TNAS (TNA containing 0.125% SDS) and once with TNE (50 mM Tris-HCl (pH 7.5), 150 mM NaCl, 1 mM EDTA, 80 μg of PMSF per ml), solubilized by heating at 80° C. for 20 min in protein sample buffer and separated on an SDS-10% polyacrylamide gel. Metabolically labeled proteins were visualized by fluorography.

Example 9

Cell Lines Permissive for HCV Replication

From 22 G418-resistant clones (Blight, K. J. 2000), clones Huh-7.5 and Huh-7.8, harboring SG-Neo subgenomic replicons with no amino acid changes within the HCV NS region, as well as clone Huh-7.4, containing a replicon with the Ser to Ile change at position 2204 in NS5A, were cured. Uncloned population lines Huh-7/S2204I and Huh-7/5AΔ47 (Blight, K. J. 2000), selected with G418 after transfection of subgenomic replicons containing either S2204I in NS5A {SG-Neo (S2204I); FIG. 1} or the 47 amino acid NS5A deletion {SG-Neo (5AΔ47); FIG. 1}, were also treated with IFN. To exclude the possibility that IFN treatment alone may alter the ability of Huh-7 cells to support HCV replication, the parental Huh-7 cells were treated with IFN in parallel. Following IFN treatment, cells were shown to lack HCV RNA by a nested RT-PCR specific for the 3' NTR where the detection limit was ~10 molecules of HCV RNA (Kolykhalov, A. A., J. Virol. 70:3363-3371) and by sensitivity to G418.

Figure 2:
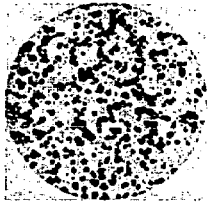
FIG. 2 shows selection of cell lines highly permissive for HCV replication.

To examine the ability of IFN-cured cell lines to support HCV replication, three G418-selectable replicons, SG-Neo (S2204I), SG-Neo (5AΔ47) and SG-Neo (wt) (FIG. 1), with G418-transduction efficiencies in parental Huh-7 cells of 10%, 0.2% and 0.0005%, respectively, were used (Blight, K. J. 2000). In vitro-synthesized RNA was electroporated into IFN-cured cells and after 48 h, G418 selection was imposed and the resulting colonies counted after fixing and staining. The transduction efficiencies were calculated on the basis of the number of G418-selected colonies relative to the number of Huh-7 cells plated after electroporation. The frequency of Huh-7.5 cells able to support SG-Neo (S2204I) replication was ~3-fold higher than the parental Huh-7 cells (FIG. 2). For cell lines Huh-7.5 and Huh-7.8, the nunber of G418-resistant colonies obtained after transfection of SG-Neo (5AΔ47) was significantly higher than for the parental Huh-7 cells (~33- and 9-fold increases, respectively; FIG. 2). The same was true for Huh-7.4, although the increased frequency of colony formation was not as great (~3-fold; FIG. 2). The SG-Neo (wt) replicon also showed an enhanced replicative capacity in Huh-7.5, Huh-7.8 and Huh-7.4 cells (10-, 2- and 2-fold increases, respectively; FIG. 2).

The two cured cell populations, Huh-7/5AΔ47 and Huh-7/ S2204I, showed either comparable or modest increases in G418 transduction efficiencies after transfection of the adapted replicon RNA originally present within the population line (FIG. 2). The frequency of G418-resistant colonies increased ~2.5-fold when Huh-7/5AΔ47 cells were electroporated with SG-Neo (5AΔ47), whereas transfection with SG-Neo (S2204I) resulted in a slight decrease in the G418 transduction efficiency (FIG. 2). However, a 23-fold reduction in colony formation was observed after transfection of Huh-7/S2204I cells with SG-Neo (5AΔ47) (FIG. 2). No significant differences in G418-resistant colony formation were noted between the parental Huh-7 cells and IFN-treated Huh-7 cells (data not shown), indicating that the IFN-mediated curing protocol did not stably influence the ability of these cells to support HCV replication. G418-resistant colonies were not observed when the polymerase defective replicon RNA, pol$^-$, was transfected in parallel (data not shown).

Hence, a higher frequency of cells in the cured clonal lines, in particular those originally able to support replication of RNAs without adaptive mutations (Huh-7.5 and Huh-7.8), are permissive for HCV replication.

Example 10

HCV Replication in Unselected Huh-7.5 and Huh-7 Cells

Figure 3:
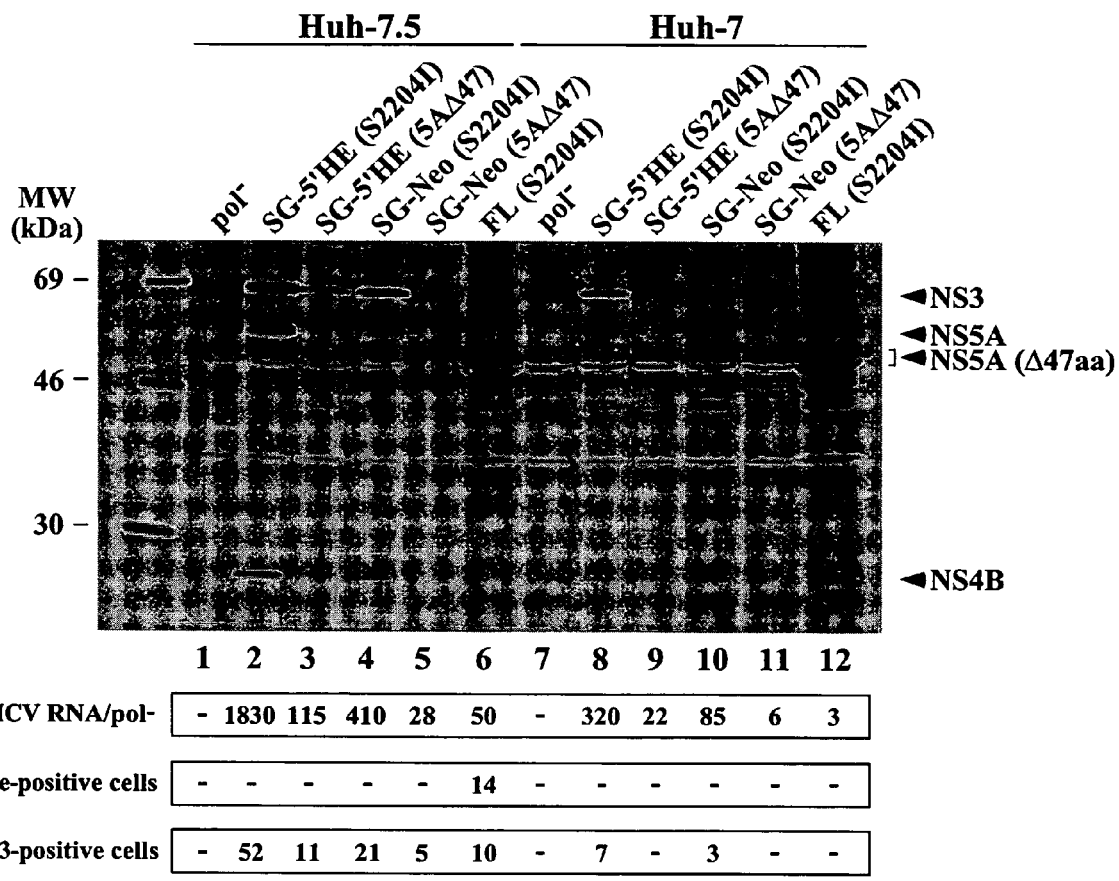
FIG. 3 shows detection of HCV proteins and RNA in Huh-7.5 and Huh-7 cells transiently transfected with HCV RNA.

Since the cured Huh-7.5 line was the most permissive of those tested, we examined HCV replication in this subline compared with the parental Huh-7 cells using a number of different methods. We focused on transient assays that would allow an assessment of HCV replication early after transfection without the need for G418 selection. Ninety-six hours after transfection with SG-Neo (S2204I) and SG-Neo (5AΔ47) RNA (FIG. 1), total RNA was extracted from Huh-7.5 and IFN-treated Huh-7 cells and the HCV RNA levels quantified by RT-PCR. The replication-defective replicon, pol$^-$, was transfected in parallel to allow discrimination between input RNA and RNA generated by productive replication. As shown in FIG. 3, the levels of HCV RNA relative to the por control were consistently higher in the transfected Huh-7.5 cells. Transfection with SG-Neo (S2204I) and SG-Neo (5AΔ47) RNAs resulted in 410- and 28-fold increases, respectively, in Huh-7.5 cells (FIG. 3, lanes 4 and 5), compared to only 85- and 6-fold in Huh-7 cells (FIG. 3, lanes 10 and 11). Since these increases are measured relative to the replication defective pol-control, they reflect accumulation of newly synthesized RNA versus degradation of input RNA. In Huh-7.5 and Huh-7 cells, the level of residual pol-RNA declined by about 10-fold at each timepoint. In Huh-7.5 cells, RNAs was good replicative abilities {like SG-Neo (S2204I)} tended to accumulate over time such that about a 10-fold increase was observed by 96 h. Those with lower replicative ability {like SG-Neo (5AΔ47)} remained constant or declined slightly, but never to the level of the pol-control. For Huh-7 cells, the picture was somewhat different. For example, SG-Neo (S2204I) RNA remained relatively constant whereas SG-Neo (5AΔ47) RNA decreased over time, but again, not to the extent of the pol– control.

This finding was mirrored by the frequency of NS3-positive cells measured by FACS analysis. The percentage of NS3-positive cells was consistently higher in Huh-7.5 cells {21% for SG-Neo (S2204I) and 5% for SG-Neo (5AΔ47); FIG. 3, lanes 4 and 5} compared to Huh-7 cells {3% for SG-Neo (S2204I) and undetectable for SG-Neo (5AΔ47) and pol$^-$ RNAs; FIG. 3, lanes 7, 10 and 11}. These results confirm our earlier conclusion that a larger fraction of Huh-7.5 cells support detectable levels of HCV replication. The lower frequency of HCV antigen-positive cells quantified by FACS compared to the G418 transduction efficiency is attributable to the sensitivity of FACS analysis, that varies with different HCV-specific antibodies (unpublished observations).

HCV protein accumulation was examined by metabolically labeling cells 96 h after transfection. Cell monolayers were labeled with $^{35}$S-methionine and -cysteine for 10 h, followed by SDS-mediated lysis and immunoprecipitation of HCV proteins with a HCV-positive patient serum (JHF) recognizing NS3, NS4B and NS5A (Grakoui, A. et al., J. Virol. 67:1385-1395). After separation of labeled proteins by SDS-PAGE, NS3, NS4B and NS5A were only visible in Huh-7.5 cells transfected with SG-Neo (S2204I) (FIG. 3, lane 4). HCV proteins were never detected in Huh-7.5 and Huh-7 cells transfected with SG-Neo (5AΔ47), pol$^-$ or SG-Neo (S2204I) RNA electroporated Huh-7 cells (FIG. 3, lanes 1, 5, 7, 10 and 11). Similar results were obtained after metabolic labeling of HCV RNA in the presence of actinomycin D (data not shown). These analyses demonstrate the advantages of using Huh-7.5 cells for rapid analysis of HCV replication by RNA accumulation, FACS analysis and metabolic labeling of viral proteins.

Example 11

Replicative Efficiencies of Subgenomic and Genomic HCV RNAs

The ability to monitor HCV replication without selection eliminated the need for bicistronic replicons and allowed constructs with minimal heterologous elements to be tested. A subgenomic replicon was engineered in which the HCV 5' NTR and 12 amino acids of core were fused to ubiquitin followed by the NS3-5B coding region (including the S2204I adaptive mutation in NS5A) and the 3' NTR {SG-5'Ub-NS3 (S2204I); FIG. 1}. In this polyprotein, cellular ubiquitin carboxyl-terminal hydrolase will cleave at the ubiquitin/NS3 junction to produce NS3 with an authentic N-terminal Ala residue (2, 21). In vitro-synthesized RNA was electroporated into Huh-7.5 and Huh-7 cells and the level of HCV RNA quantified 96 h later by RT-PCR. Surprisingly, HCV RNA levels did not differ from the por control (data not shown), indicating that SG-5'Ub-NS3 (S2204I) RNA failed to replicate. It is possible that ubiquitin may interfere with the production of a functional NS3 protein. However, a bicistronic derivative, where expression of ubiquitin/NS3-5B was under the control of the EMCV IRES, replicated as efficiently as SG-Neo (S2204I) RNA (data not shown), suggesting that HCV IRES driven translation may be sensitive to RNA elements present within the core-ubiquitin coding sequence.

Figure 4:
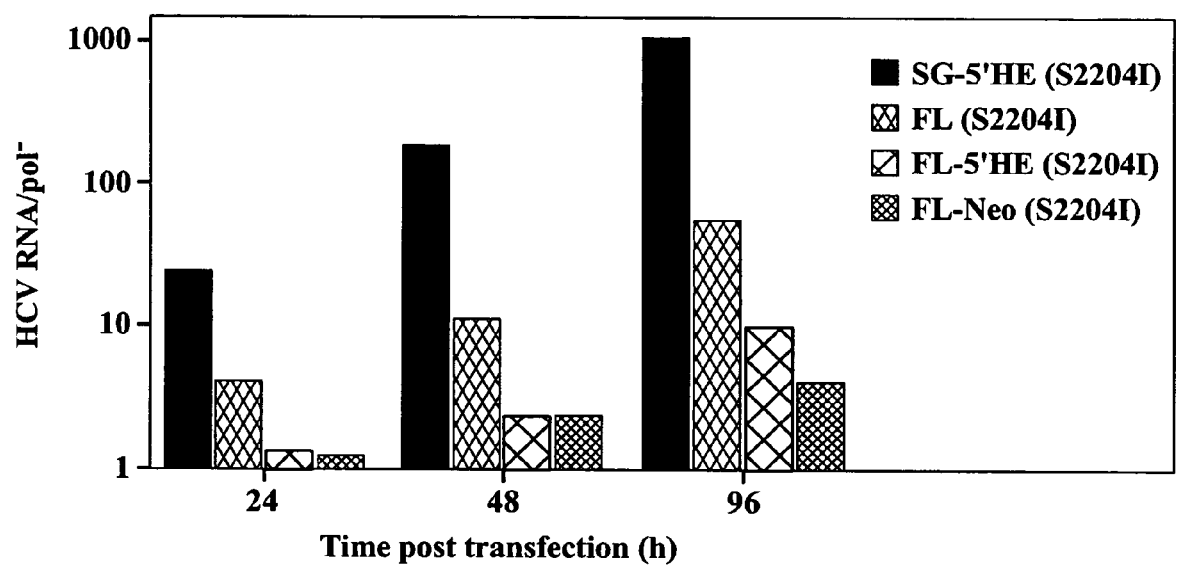
FIG. 4 shows HCV RNA accumulation after transfection of Huh-7.5 cells with full-length HCV RNA.

A replicon lacking neo but retaining the EMCV IRES (SG-5'HE derivatives; FIG. 1) was also tested. SG-5'HE (S2204I) and SG-5'HE (5AΔ47) RNA levels relative to the pol$^-$ control were measured 96 h after transfection and found to be higher than the selectable versions in both Huh-7.5 and Huh-7 cells (FIG. 3). Moreover, the levels of SG-5'HE (S2204I) and SG-5'HE (5AΔ47) RNA were significantly higher in Huh-7.5 compared to Huh-7 cells (FIG. 3, lanes 2, 3, 8 and 9). Approximately 52% of Huh-7.5 cells stained positive for the NS3 antigen after transfection of SG-5'HE (S2204I) RNA, compared to 21% for SG-Neo (S2204I) RNA (FIG. 3, lanes 2 and 4). Similarly, a higher frequency of Huh-7.5 cells expressed NS3 after electroporation with SG-5'HE (5AΔ47) compared to SG-Neo (5AΔ47) (11% versus 5%; FIG. 3, lanes 3 and 5). As expected, lower frequencies of NS3-positive cells were observed for transfected Huh-7 cells (FIG. 3). The relative amounts of immunoprecipitated $^{35}$S-labeled HCV proteins from Huh-7.5 and Huh-7 cells paralleled both the frequency of NS3-positive cells and relative HCV RNA levels (FIG. 3). These data demonstrate that replicons lacking the neo gene initiate RNA replication more efficiently. These constructs, together with the highly permissive Huh-7.5 subline, are valuable tools for genetic studies on HCV RNA replication, some of which are described later in this report. The ability of Huh-7.5 cells to support replication of full-length HCV RNA containing S2204I in NS5A {FL (S2204I); FIG. 1} was also assessed. Ninety-six hours after transfection of Huh-7.5 and Huh-7 cells, the relative levels of HCV RNA and protein were measured as described above. A 50-fold increase in HCV RNA relative to pol$^-$ was observed after transfection of Huh-7.5 cells, compared to only a 3-fold increase in Huh-7 cells (FIG. 3, lanes 6 and 12). Similarly, FACS analysis and immunoprecipitation of metabolically labeled proteins failed to detect HCV antigen expression in FL RNA transfected Huh-7 cells, whereas 14% and 10% of Huh-7.5 cells expressed core and NS3 antigens, respectively, and $^{35}$S-labeled NS3 was detectable (FIG. 3, lanes 6 and 12). The frequency of core-antigen positive cells was consistently higher than that seen for NS3, possibly reflecting differences in antibody affinity. The ability of full-length HCV RNA to establish replication in Huh-7.5 cells demonstrates that replication is not dependent upon EMCV IRES-driven translation of HCV-encoded replicase components. In fact, inclusion of the EMCV IRES downstream of the HCV 5' NTR {FL-5'HE (S2204I); FIG. 1} or creation of a biscistronic construct with the neo gene added {FL-Neo (S2204I); FIG. 1} impaired replication relative to FL (2204I) RNA (FIG. 4). It is interesting to note that all of the constructs containing the complete HCV coding sequence (S2204I-containing FL, FL-5'HE and FL-Neo) were less efficient at establishing replication compared to subgenomic replicons lacking the structural-NS2 coding region {eg. SG-5'HE (S2204I); FIG. 4}. This suggests that cis RNA elements or proteins encoded in this region of the genome may downregulate the efficiency of HCV replication in this system. Nonetheless, the ability of Huh-7.5 cells to support replication of both FL and FL-Neo RNAs provides systems that may be useful for studying steps in particle assembly and examining the impact of the entire HCV protein complement on host cell biology.

Example 12

Effect(s) of Mutations in NS3 and NS5A on HCV RNA Replication

Figure 5:
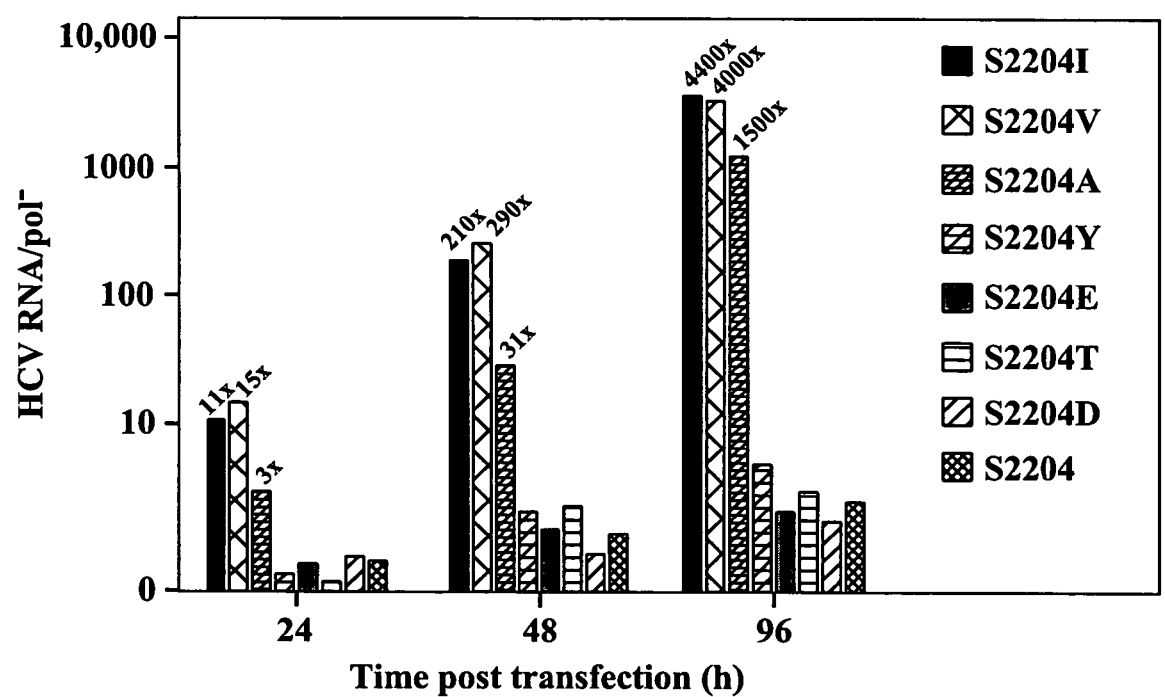
FIG. 5 shows effects of alternative substitutions at position 2204 on HCV RNA replication.

Thus far, the best single mutation that has been identified is the S2204I substitution in NS5A. To examine the importance of Ile at this position and to see if replication efficiency could be improved further, a number of other amino acids were tested at this position and compared the replication efficiency of these replicons to SG-5'HE (S2204I) or the unmodified parent, SG-5'HE (S2204) (FIG. 5). Replicative ability was assessed in RNA transfected Huh-7.5 cells by comparing the HCV RNA levels to a SG-pol-control. Comparable levels of HCV RNA were observed at 96 h for replicons containing Ile or Val at position 2204, whereas an Ala substitution resulted in a 3-fold reduction in HCV RNA compared to SG-5'HE (S2204I) (FIG. 5). In contrast, the remaining amino acid substitutions dramatically reduced HCV RNA to levels similar to the unmodified parental replicon, SG-5'HE (S2204) (~1400-fold decrease; FIG. 5). As expected, the relative HCV RNA levels were lower at 24 and 48 h after transfection, however the levels were sufficient to assess replicative ability at 48 h (FIG. 5). Although substitutions that enhance subgenomic replication above that observed with S2204I were not found, Val and Ala allowed efficient RNA replication.

Figure 6:
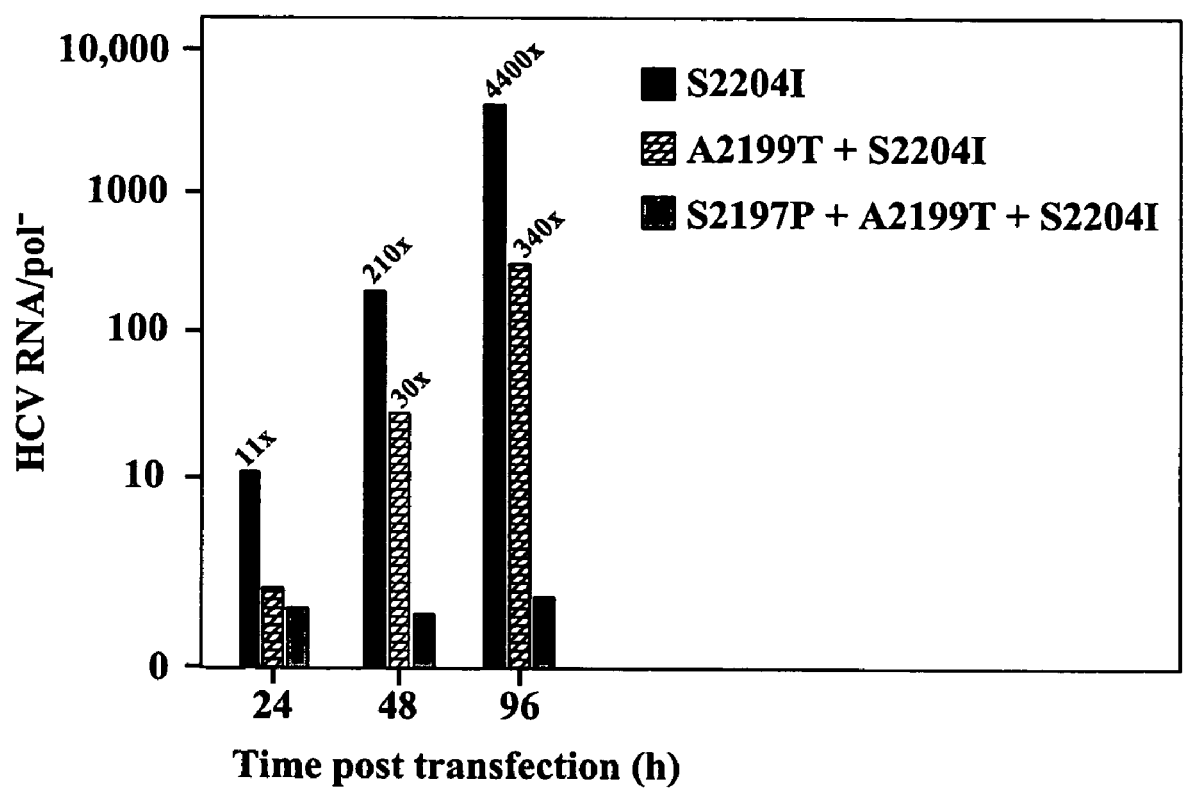
FIG. 6 shows effects of combining NS5A adaptive mutations on HCV Rna replication.

The replication efficiency of subgenomic replicons carrying multiple adaptive mutations in NS5A was investigated. NS5A mutations S2197P, A2199T and S2204I independently enhance G418-resistant colony formation approximately 2,500-, 15,000- and 20,000-fold, respectively (5). SG-5'HE replicons (FIG. 1) carrying S2204I together with either A2199T, or A2199T and S2197P were constructed and HCV RNA levels in Huh-7.5 cells measured by RT-PCR. Combining these NS5A mutations led to a reduction in HCV RNA levels compared to SG-5'HE (S2204I), with a 13-fold decrease for the combination of A2199T and S2204I and negligible replication when all three were combined (FIG. 6).

Despite the observation that each of these NS5A adaptive mutations alone enhanced replication, when combined, the replicative ability of subgenomic RNAs declined, suggesting that these combinations are incompatible.

Figure 7A:
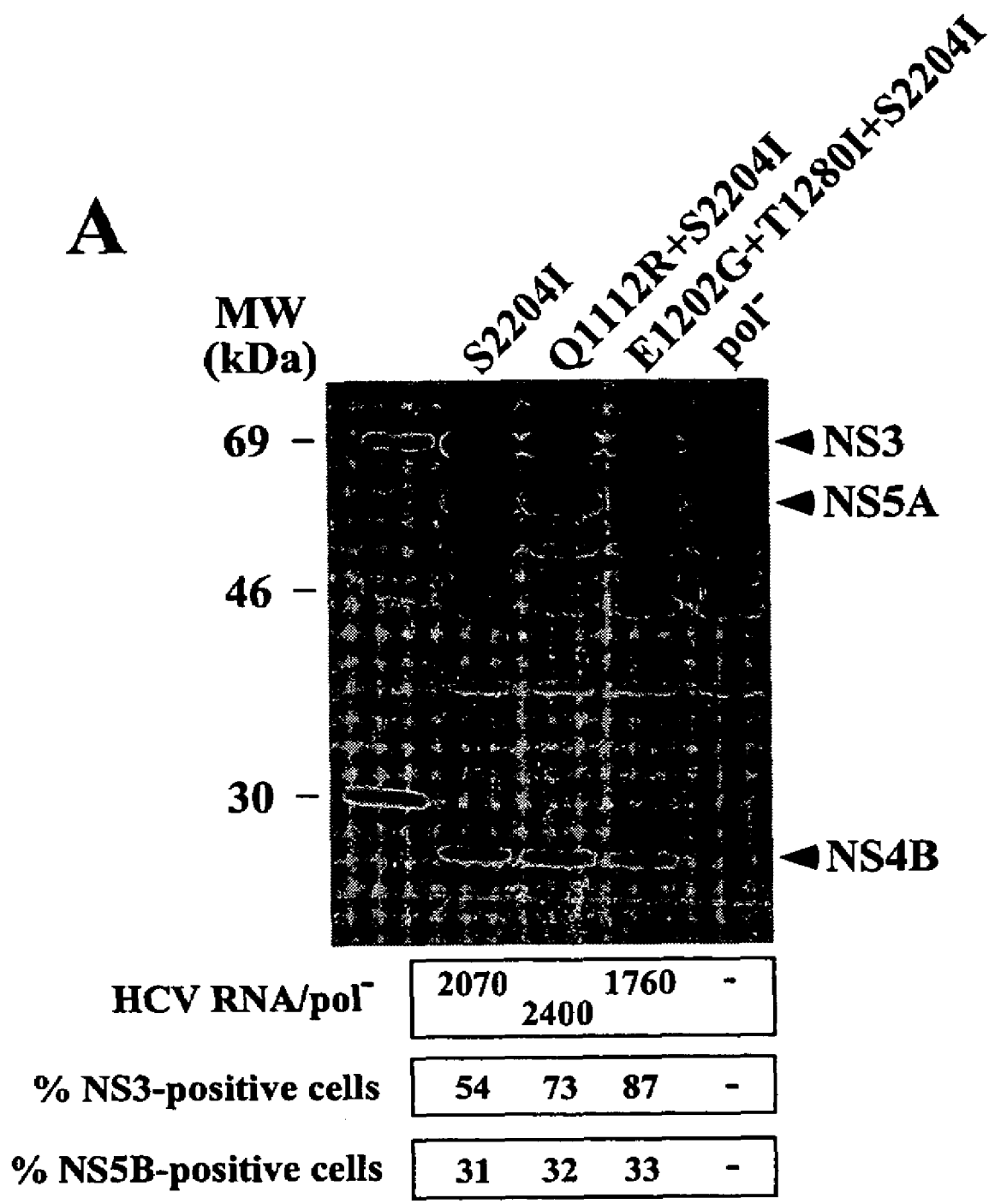
FIG. 7 shows effects of combining NS3 and NS5A mutations on HCV replication.
Figure 7B:
Figure 7B:
Figure 7B:
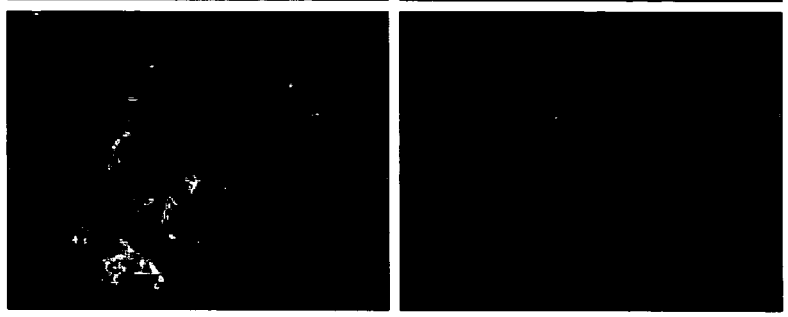
Figure 7B:
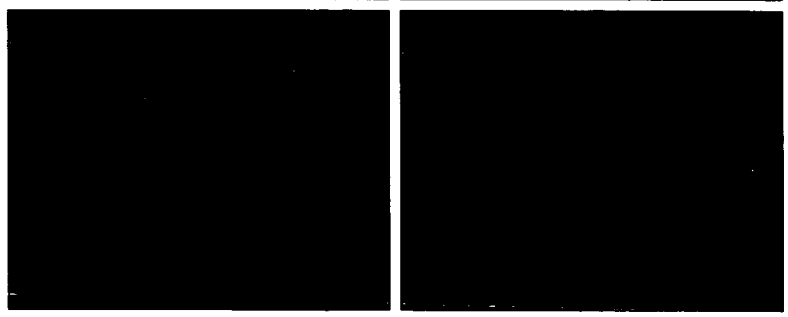

NS3 changes at positions 1112 (Q to R), 1202 (E to G) and 1280 (T to I) were engineered into SG-5'HE (S2204I) (FIG. 1) and their replication compared in Huh-7.5 cells by measuring HCV RNA levels, the frequency of antigen-positive cells and by detection of $^{35}$S-labeled proteins at 96 h following transfection. Equivalent levels of HCV RNA relative to the pol⁻ RNA control were observed for each replicon (FIG. 7A). The percentage of NS5B-positive cells detected by FACS (~30%; FIG. 7A) and immunofluorescence (FIG. 7B) was also similar. However, the frequency of NS3-positive cells was higher for replicons carrying the NS3 mutations (~73-87%; FIG. 7A), which may simply reflect altered affinity of the NS3-specific antibody for these NS3 mutants. Finally, the levels of immunoprecipitated NS3, NS4B and NS5A were comparable (FIG. 7A). Although it was not verified that Q1112R alone was adaptive, Krieger and coworkers previously reported that E1202G and T1280I alone or together increased the replication efficiency by ~13-, 6- and 25-fold, respectively (Krieger et al. 2001). These NS3 adaptive mutations do not further enhance replication when combined with S2204I in NS5A.

Example 13

Mutagenesis of the S2194 NS5A Phosphorylation Site

Figure 8A:
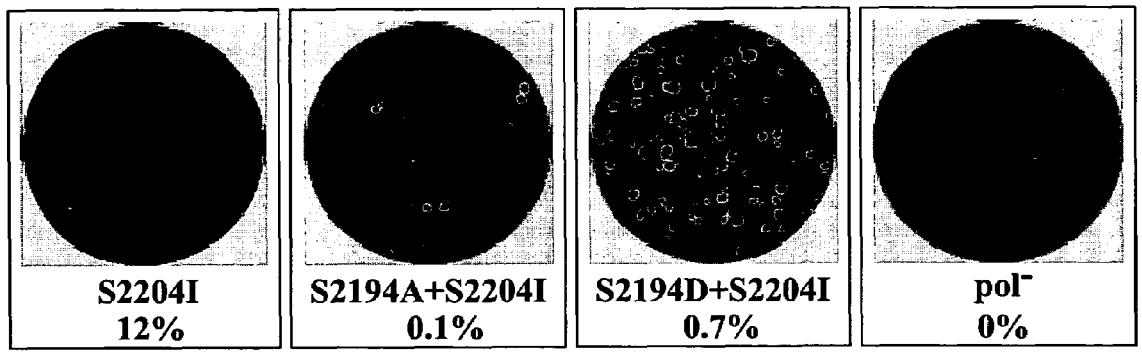
FIG. 8 shows effect of S2194A and S2194D mutations on HCV RNA replication.
Figure 8B:
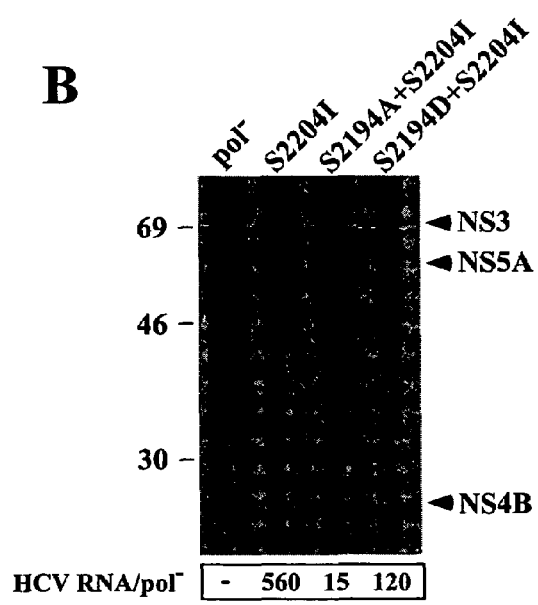

The role of NS5A phosphorylation in HCV replication remains a mystery. Previously, differences were noted in the extent of NS5A phosphorylation between replicons with different adaptive mutations in NS5A (Blight et al. 2000). For example, replicons with S2197C, S2197P or S2204I expressed minimal or no p58 as assessed by one-dimensional SDS-PAGE separation of immunoprecipated NS5A, suggesting that NS5A hyperphosphorylation is not essential for HCV replication. Recently, S2194 in NS5A of a subtype 1b isolate was identified as the-primary site of p56 phosphorylation (Katze et al. 2000). To assess the possible requirement for phosphorylation of NS5A S2194, this residue was mutated in SG-Neo (S2204I) (FIG. 1) to either Ala (S2194A+S2204I) or Asp (S2194D+S2204I), to ablate or mimic phosphorylation, respectively. G418 transduction efficiencies of these replicons in Huh-7 cells was significantly lower than SG-Neo (S2204I) (120- and 17-fold lower; FIG. 8A). To rule out the possibility that G418-resistant foci were generated by reversion at this locus, the NS5A coding region was amplified from total cellular RNA by RT-PCR and directly sequenced. The original Ala and Asp substitutions at position 2194 were confirmed (data not shown). To minimize the impact of possible second site compensating changes, HCV RNA and protein expression was measured 96 h after RNA transfection of Huh-7.5 cells. The HCV RNA levels of S2194A+S2204I and S2194D+S2204I relative to the pol control were ~37- and 5-fold lower than SG-Neo (S2204I) (FIG. 8B), consistent with their reduced ability to render Huh-7 cells G418 resistant. In addition, a lower frequency of NS5B-positive cells was evident in S2194A+S2204I than in S2194D+S2204I (data not shown), and $^{35}$S-labeled NS3 and NS4B were only detectable in Huh-7.5 cells transfected with SG-Neo (S2204I) and S2194D+S2204I (FIG. 8B). It was not possible to directly study the phosphorylation status of NS5A expressed from S2194A+S2204I and S2194D+S2204I since the levels of NS5A expressed in transiently transfected cells were below the detection limit (FIG. 8B and data not shown).

Although the quantitative differences in G418 transduction and replication efficiencies are difficult to interpret given the possible incompatibility of combining the S2194 substitutions with the S2204I adaptive change, these data show that phosphorylation of S2194 is not an absolute requirement for HCV replication.

Figure Legends

FIG. 1. Schematic representation of HCV RNAs used in this study. The 5' and 3' NTR structures are shown and ORFs depicted as open boxes with the polyprotein cleavage products indicated. The first 12 amino acids of the core-coding region (solid box), the neo gene (Neo; shaded box), the EMCV IRES (EMCV; solid line) and ubiquitin (hatched box) are illustrated. Locations of the NS5A adaptive mutations S2204I (*) and Δ47aa are indicated.

FIG. 2. Identification of Huh-7 lines highly permissive for HCV replication. Huh-7 cells that had been cured of self-replicating subgenomic RNAs by extended IFN treatment were electroporated with 1 μg of the subgenomic replicons, SG-Neo (S2204I), SG-Neo (5AΔ47) and SG-Neo (wt). Forty-eight hours later, cells were subjected to G418 selection and the resulting colonies fixed and stained with crystal violet. Representative plates are illustrated with the number of transfected cells seeded per 100-mm diameter dish shown on the left. Numbers below each dish refer to the calculated G418 transduction efficiency of the replicon. To determine the G418 transduction efficiency, transfected cells were serially titrated from $5 \times 10^5$ to $10^3$ cells per 100-mm diameter dish, together with feeder cells electroporated with the pol$^-$ replicon. The resulting G418-resistant foci were counted-for at least 3 cell densities and the relative G418 transduction efficiency expressed as a percentage, after dividing the number of colonies by the number of electroporated cells initially plated. Similar transduction efficiencies were obtained in two independent transfections. A poliovirus subgenomic replicon expressing GFP (see Methods) was electroporated in parallel. Based on both the fraction of GFP-positive cells and replicon-induced cytopathogenicity, ~90% of cells were routinely transfected. NT=not tested FIG. 3. Detection of HCV proteins and RNA in Huh-7.5 and Huh-7 cells transiently transfected with HCV RNA. Top panel, Huh-7.5 and Huh-7 cells were transfected with the subgenomic replicons, pol$^-$ (lanes 1 and 7), SG-5'HE (S2204I) (lanes 2 and 8), SG-5'HE (5AΔ47) (lanes 3 and 9), SG-Neo (S2204I) (lanes 4 and 10), SG-Neo (5AΔ47) (lanes 5 and 11) and FL (S2204I) HCV RNA (lanes 6 and 12). At 96 h posttransfection, monolayers were incubated for 10 h in the presence of $^{35}$S-methionine and -cysteine. Labeled cells were lysed, immunopreciptated with HCV-positive human serum (JHF, anti-NS3, NS4B and NS5A) and labeled proteins separated by SDS-10% PAGE. Note that twice the amount of immunopreciptated sample was loaded in lanes 6 and 12 (2×). The mobilities of molecular mass standards (MW) are indicated on the left and the migration of NS3, NS4B, NS5A and 5AΔ47 are shown on the right. Middle panel, Total cellular RNA was extracted at 96 h posttransfection and quantified for HCV RNA levels as described in the Materials and Methods. The ratio of HCV RNA relative to the pol$^-$ defective replicon is shown (HCV RNA/pol). HCV RNA levels relative to the por control were comparable in three independent experiments. Lower two panels, 96 h after transfection cells were fixed with 4% paraformaldehyde, permeabilized with 0.1% saponin, stained for either HCV core or NS3 antigens and analyzed by FACS. The percentage of cells expressing core and NS3 relative to an isotype matched irrelevant IgG is displayed. Values <1.5% were considered negative (−).

FIG. 4. HCV RNA accumulation after transfection of Huh-7.5 cells with full-length HCV RNA. One-μg of in vitro transcribed RNA was electroporated into Huh-7.5 and $2 \times 10^5$ cells plated into 35-mm diameter wells. Total cellular RNA was isolated at 24, 48 and 96 h posttransfection and HCV RNA levels quantified as described in the Materials and Methods. The ratio of HCV RNA relative to the pol$^-$ defective subgenomic RNA (HCV RNA/pol$^-$) was plotted against the time posttransfection and similar results were obtained when this experiment was repeated FIG. 5. Effects of alternative substitutions at position 2204 on HCV RNA replication. Huh-7.5 cells were transfected with 1 μg of the SG-5'HE replicons carrying the indicated amino acid substitutions and $2 \times 10^5$ cells plated in 35-mm diameter wells. After 24, 48 and 96 h in culture, total cellular RNA was extracted and HCV RNA levels measured as described in the Materials and Methods. The ratio of HCV RNA relative to the pol$^-$ defective subgenomic RNA (HCV RNA/pol$^-$) was plotted against the time posttransfection. The increase in HCV RNA above pol$^-$ is indicated above each bar. In this figure the levels of HCV RNA relative to the pol$^-$ are the highest we have achieved so far. When these RNAs were transfected into Huh-7.5 cells a second time a similar trend in HCV RNA accumulation was observed.

FIG. 6. Effect(s) of combining NS5A adaptive mutations on HCV RNA replication. Subgenomic replicons were transfected into Huh-7.5 cells and HCV RNA levels quantitated as described in FIG. 5. The ratio of HCV RNA relative to the pol$^-$ defective subgenomic RNA (HCV RNA/pol$^-$) was plotted against the time posttransfection and the increase in HCV RNA above pol$^-$ is indicated above each bar. An additional transfection experiment yielded HCV RNA/por ratios similar to those illustrated here.

FIG. 7. Effect(s) of combining NS3 and NS5A mutations on HCV RNA replication. Subgenomic replicons lacking neo were generated carrying S2204I with further mutations in NS3. (A) Top, 96 h after RNA transfection of Huh-7.5 cells, monolayers were labeled with $^{35}$S-protein labeling mixture, lysed and NS3, NS4A and NS5A analyzed by immunoprecipitation, SDS-10% PAGE and autoradiography. Positions of the molecular weight standards are given on the left and HCV-specific proteins indicated to the right. Middle, Total cellular RNA was extracted at 96 h posttransfection and HCV RNA levels quantified as described in the Materials and Methods. The ratio of HCV RNA relative to the pol$^-$ negative control is shown (HCV RNA/pol$^-$). Comparable ratios were obtained in two independent experiments. Lower two panels, 96 h after transfection, cells were fixed with 4% paraformaldehyde, permeabilized with 0.1% saponin, stained for HCV NS3 and NS5B antigens and analyzed by FACS. The percentage of cells expressing NS3 and NS5B relative to an isotype matched irrelevant IgG is displayed. Values <1.5% were considered negative (−). (B) Transfected cells seeded in eight-well chamber slides were fixed, permeablized and stained for NS5B by immnunofluorescence after 96 h in culture. Nuclei were counterstained with Hoescht 33342 and stained cells visualized by fluorescent microscopy (×40 magnification).

FIG. 8. Effect of S2194A and S2194D mutations on HCV RNA replication. S2194 was replaced with Ala or Asp in the selectable bicistronic replicon SG-Neo (S2204I) and RNA transcribed in vitro. (A) RNA transcripts were transfected into Huh-7 cells and G418-selected colonies fixed and stained with crystal violet. The relative G418 transduction efficiencies are indicated below each dish. (B) Ninety-six hours post-transfection Huh-7.5 cells were labeled with $^{35}$S-methionine and -cysteine for 10 h. Cells were lysed, and HCV proteins isolated by immunoprecipitation using a patient serum specific for NS3, NS4B and NS5A. HCV proteins and the positions of protein molecular weight standards (in kilodaltons) are shown. The ratio of HCV RNA relative to the pol⁻ negative control at 96 h posttransfection is shown below each track (HCV RNA/pol⁻). The results illustrated are representative of two independent transfections.

As various modifications could be made in the constructions and methods herein described and illustrated without departing from the scope of the invention, it is intended that all matter contained in the foregoing description or shown in the accompanying drawings shall be interpreted as illustrative rather than limiting. Thus, the breadth and scope of the present invention should not be limited by any of the above-described exemplary embodiments.

TABLE 1

Oligodeoxynucleotides used in this study.

| Name | Sequence (SEQ ID NO) |
|---|---|
| 885 | (−) CCCTCTAGAACGCCCCGAAACCTAGGGTGGCG (SEQ ID NO:4) |
| 1030 | (−) CCCTCTAGACTCGAGGGAATTTCCTGGAC (SEQ ID NO:5) |
| 1184 | (+) GACGGCTAAGCGTAGGCTGGCCAGGGGATCTCCC CCCTCCTTGGCCAGCTCATCAGCTGACCAGCTGTCTG CGCCTTCC (SEQ ID NO:6) |
| 1287 | (+) AGACCGTGCACCAGACCACAACGGTTTCCCTCTA GCGGGATCAATTCCG SEQ ID NO:7) |
| 1288 | (−) CCAGTAACGTTAGGGGGGGGGAGGGAGAGGGGC GGAATTGATCCCGCT (SEQ ID NO:8) |
| 1289 | (+) CCAAAGGGCGCGCCATGCAGATCTTCGTGAAGACC 3' (SEQ ID NO:9) |
| 1290 | (−) AATAGGAGCTCCACCGCGGAGACGC (SEQ ID NO:10) |
| 1291 | (+) CGGTGGAGCTCCTATTACGGCCTACTCCCAAC (SEQ ID NO:11) |
| 1292 | (−) ATTGGTGTACATTTGGGTGATTGG (SEQ ID NO:12) |
| 1293 | (+) TCTGGAAGCTTCTTGAAGACA (SEQ ID NO:13) |
| 1294 | (−) GGCTTGACGTCCTGTGGGCGGCGGTTGGTGTTACGT TTGGTTTTTCTTTGAGGTTTAGGATTCGTGCTCATTATTATCG TGTTTTTCAAAGG (SEQ ID NO:14) |

TABLE 1-continued

Oligodeoxynucleotides used in this study.

| Name | Sequence (SEQ ID NO) |
|---|---|
| 1319 | (+) AGACGGCTAAGCGTAGGCTGGCCAGGGGATCTCCC CCCTCCTTGGCCAGCTCATCAGCTTGTACAGCTGT CTGCGCCTTCC (SEQ ID NO:15) |
| 1320 | (+) AGACGGCTAAGCGTAGGCTGGCCAGGGGATCTCC CCCCTCCTTGGCCAGCTCATCAGCTGCCCAGCTGTCTGC GCCTTCC (SEQ ID NO:16) |
| 1322 | (+) AGACGGCTAAGCGTAGGCTGGCCAGGGGATCTCCC CCCTCCTTGGCCAGCTCATCAGCTTACCAGCTGTCTGC GCCTTCC (SEQ ID NO:17) |
| 1324 | (+) AGACGGCTAAGCGTAGGCTGGCCAGGGGATCTCCC CCCTCCTTGGCCAGCTCATCAGCTGAACAGCTGTCTG CGCCTTCC (SEQ ID NO:18) |
| 1325 | (+) AGACGGCTAAGCGTAGGCTGGCCAGGGGATCTCCC CCCTCCTTGGCCAGCTCATCAGCTACACAGCTGTCTG CGCCTTCC (SEQ ID NO:19) |
| 1326 | (+) AGACGGCTAAGCGTAGGCTGGCCAGGGGATCTCCC CCCTCCTTGACCAGCTCATCAGCTATCCAGCTGTCTG CGCCTTCC (SEQ ID NO:20) |
| 1327 | (+) AGACGGCTAAGCGTAGGCTGGCCAGGGGATCTCCC CCCCCCCTTGACCAGCTCATCAGCTATCCAGCTGTCT GCGCCTTCC (SEQ ID NO:21) |
| 1356 | (−) CCGCTCTAGATACGTGATGGGGGCACCCGTGGTG ATGGTCCTTACCCCGATTCTGATGTTAGGG TCGATAC (SEQ ID NO:22) |
| 1358 | (+) CCGATGTACACCAATGTGGACCAGGACCTCGTCG GCTGGCGAGCGCCCCCCGGGGCGCGTTCC (SEQ ID NO:23) |
| 1359 | (+) CCGCGTGCACCCGAGGGGTTGCGAAGGCGGTGGA CTTTGTACCCGTCGAGTCTATGGGAACCACTATGC GGTCCCCGGTC (SEQ ID NO:24) |
| 5'Ala | (+) CCACGCTAAGCGTAGGCTGGCCAGGGGAGCA CCCCCCTCCTTGGCCAGCTC (SEQ ID NO:25) |
| 5'Asp | (+) CCACGCTAAGCGTAGGCTGGCCAGGGGA GATCCCCCCTCCTTGGCCAGCTC (SEQ ID NO:26) |

ᵃNucleotide changes are highlighted in bold and the resultant codon is underlined
ᵇRestriction sites used for cDNA cloning are underlined
ᶜThe polarities of oligonucleotides are indicated either the HCV genome RNA sense (+) or its complement (−)

What is claimed is:

1. A method for producing a cell line permissive for HCV replication, the method comprising:
   (a) providing an Huh-7.5 cell line on deposit with the ATCC as accession number PTA-8561 that further comprises a genomic or subgenomic HCV RNA capable of replication;
   (b) obtaining a culture of said cell line that supports replication of said genomic or subgenomic HCV RNA;
   (c) curing said cell line of (b) of HCV RNA, wherein said curing comprises treatment with an antiviral agent; and
   (d) identifying sublines of said cured cell line of (b) that are permissive for HCV replication.

2. The method of claim 1, wherein said agent is an antiviral cytokine.

3. The method of claim 2, wherein said antiviral cytokine is interferon.

4. The method of claim 1, wherein said cell line of (a) comprises a replicating subgenomic HCV RNA containing no adaptive mutations.

5. The method of claim 1, wherein said cell line of (a) comprises a replicating subgenomic HCV RNA that comprises an adaptive mutation.

6. An Huh-7.5 cell line on deposit with the ATCC as accession number PTA-8561.

7. The cell line of claim 6, wherein said cell line contains subgenomic HCV RNA.

8. The cell line of claim 7, wherein said subgenomic HCV RNA comprises an adaptive mutation.

9. The cell line of claim 8, wherein said adaptive mutation is S2204I, S2204V, or S2204A, said position being identified by alignment with the genotype 1 b Con1 full-length HCV genome (SEQ ID NO:27) commencing with the core-coding region.

10. The cell line of claim 6, wherein said cell line contains genomic HCV RNA.

11. The cell line of claim 10, wherein said genomic HCV RNA comprises an adaptive mutation.

12. The cell line of claim 11, wherein said adaptive mutation is S2204I, S2204V, or S2204A, said position being identified by alignment with the genotype 1b Con1 full-length HCV genome (SEQ ID NO:27) commencing with the core-coding region.

* * * * *

SEQUENCE LISTING

<160> NUMBER OF SEQ ID NOS: 27

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 1
cctctagagc catagtggtc t                                          21

```
<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ccaaatctcc aggcattgag c                                             21

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
caccggaatt gccaggacga ccgg                                          24

<210> SEQ ID NO 4
<211> LENGTH: 32
<212> TYPE: DNA
<213> ORGANISM: Artificial Sequence
<220> FEATURE:
<223> OTHER INFORMATION: Description of Artificial Sequence: Synthetic
      oligodeoxynucleotide

<400> SEQUENCE: 4
ccctctagaa cgccccgaaa cctagggtgg cg                                 32

<210> SEQ ID NO 5
<211> LENGTH: 29
<212> TYPE: DNA
<213> ORGANISM: Artificial Sequence
<220> FEATURE:
<223> OTHER INFORMATION: Description of Artificial Sequence: Synthetic
      oligodeoxynucleotide

<400> SEQUENCE: 5
ccctctagac tcgagggaat ttcctggac                                     29

<210> SEQ ID NO 6
<211> LENGTH: 79
<212> TYPE: DNA
<213> ORGANISM: Artificial Sequence
<220> FEATURE:
<223> OTHER INFORMATION: Description of Artificial Sequence: Synthetic
      oligodeoxynucleotide

<400> SEQUENCE: 6
gacggctaag cgtaggctgg ccagggatc tcccccctcc ttggccagct catcagctga    60
ccagctgtct gcgccttcc                                                79

<210> SEQ ID NO 7
<211> LENGTH: 49
<212> TYPE: DNA
<213> ORGANISM: Artificial Sequence
<220> FEATURE:
<223> OTHER INFORMATION: Description of Artificial Sequence: Synthetic
      oligodeoxynucleotide

<400> SEQUENCE: 7
agaccgtgca ccagaccaca acggtttccc tctagcggga tcaattccg               49
```

<210> SEQ ID NO 8
<211> LENGTH: 49
<212> TYPE: DNA
<213> ORGANISM: Artificial Sequence
<220> FEATURE:
<223> OTHER INFORMATION: Description of Artificial Sequence: Synthetic
      oligodeoxynucleotide

<400> SEQUENCE: 8
ccagtaacgt tagggggggg ggagggagag gggcggaatt gatcccgct           49

<210> SEQ ID NO 9
<211> LENGTH: 35
<212> TYPE: DNA
<213> ORGANISM: Artificial Sequence
<220> FEATURE:
<223> OTHER INFORMATION: Description of Artificial Sequence: Synthetic
      oligodeoxynucleotide

<400> SEQUENCE: 9
ccaaagggcg cgccatgcag atcttcgtga agacc                         35

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: Synthetic
      oligodeoxynucleotide

<400> SEQUENCE: 10
aataggagct ccaccgcgga gacgc                                    25

<210> SEQ ID NO 11
<211> LENGTH: 32
<212> TYPE: DNA
<213> ORGANISM: Artificial Sequence
<220> FEATURE:
<223> OTHER INFORMATION: Description of Artificial Sequence: Synthetic
      oligodeoxynucleotide

<400> SEQUENCE: 11
cggtggagct cctattacgg cctactccca ac                            32

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      oligodeoxynucleotide

<400> SEQUENCE: 12
attggtgtac atttgggtga ttgg                                     24

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      oligodeoxynucleotide

<400> SEQUENCE: 13
tctggaagct tcttgaagac a                                        21

```
<210> SEQ ID NO 14
<211> LENGTH: 92
<212> TYPE: DNA
<213> ORGANISM: Artificial Sequence
<220> FEATURE:
<223> OTHER INFORMATION: Description of Artificial Sequence: Synthetic
      oligodeoxynucleotide

<400> SEQUENCE: 14
ggcttgacgt cctgtgggcg gcggttggtg ttacgtttgg ttttctttg aggtttagga    60 ttcgtgctca ttattatcgt gttttcaaa gg                                   92

<210> SEQ ID NO 15
<211> LENGTH: 80
<212> TYPE: DNA
<213> ORGANISM: Artificial Sequence
<220> FEATURE:
<223> OTHER INFORMATION: Description of Artificial Sequence: Synthetic
      oligodeoxynucleotide

<400> SEQUENCE: 15
agacggctaa gcgtaggctg gccaggggat ctcccccctc cttggccagc tcatcagctg    60
tacagctgtc tgcgccttcc                                                80

<210> SEQ ID NO 16
<211> LENGTH: 80
<212> TYPE: DNA
<213> ORGANISM: Artificial Sequence
<220> FEATURE:
<223> OTHER INFORMATION: Description of Artificial Sequence: Synthetic
      oligodeoxynucleotide

<400> SEQUENCE: 16
agacggctaa gcgtaggctg gccaggggat ctcccccctc cttggccagc tcatcagctg    60
cccagctgtc tgcgccttcc                                                80

<210> SEQ ID NO 17
<211> LENGTH: 80
<212> TYPE: DNA
<213> ORGANISM: Artificial Sequence
<220> FEATURE:
<223> OTHER INFORMATION: Description of Artificial Sequence: Synthetic
      oligodeoxynucleotide

<400> SEQUENCE: 17
agacggctaa gcgtaggctg gccaggggat ctcccccctc cttggccagc tcatcagctt    60
accagctgtc tgcgccttcc                                                80

<210> SEQ ID NO 18
<211> LENGTH: 80
<212> TYPE: DNA
<213> ORGANISM: Artificial Sequence
<220> FEATURE:
<223> OTHER INFORMATION: Description of Artificial Sequence: Synthetic
      oligodeoxynucleotide

<400> SEQUENCE: 18
agacggctaa gcgtaggctg gccaggggat ctcccccctc cttggccagc tcatcagctg    60
aacagctgtc tgcgccttcc                                                80

<210> SEQ ID NO 19
<211> LENGTH: 80
<212> TYPE: DNA
```

<213> ORGANISM: Artificial Sequence
<220> FEATURE:
<223> OTHER INFORMATION: Description of Artificial Sequence: Synthetic
      oligodeoxynucleotide

<400> SEQUENCE: 19
agacggctaa gcgtaggctg gccaggggat ctcccccctc cttggccagc tcatcagcta      60
cacagctgtc tgcgccttcc                                                  80

<210> SEQ ID NO 20
<211> LENGTH: 80
<212> TYPE: DNA
<213> ORGANISM: Artificial Sequence
<220> FEATURE:
<223> OTHER INFORMATION: Description of Artificial Sequence: Synthetic
      oligodeoxynucleotide

<400> SEQUENCE: 20
agacggctaa gcgtaggctg gccaggggat ctcccccctc cttgaccagc tcatcagcta      60
tccagctgtc tgcgccttcc                                                  80

<210> SEQ ID NO 21
<211> LENGTH: 80
<212> TYPE: DNA
<213> ORGANISM: Artificial Sequence
<220> FEATURE:
<223> OTHER INFORMATION: Description of Artificial Sequence: Synthetic
      oligodeoxynucleotide

<400> SEQUENCE: 21
agacggctaa gcgtaggctg gccaggggat ctccccccccc cttgaccagc tcatcagcta     60
tccagctgtc tgcgccttcc                                                  80

<210> SEQ ID NO 22
<211> LENGTH: 71
<212> TYPE: DNA
<213> ORGANISM: Artificial Sequence
<220> FEATURE:
<223> OTHER INFORMATION: Description of Artificial Sequence: Synthetic
      oligodeoxynucleotide

<400> SEQUENCE: 22
ccgctctaga tacgtgatgg gggcacccgt ggtgatggtc cttaccccga ttctgatgtt      60
agggtcgata c                                                           71

<210> SEQ ID NO 23
<211> LENGTH: 63
<212> TYPE: DNA
<213> ORGANISM: Artificial Sequence
<220> FEATURE:
<223> OTHER INFORMATION: Description of Artificial Sequence: Synthetic
      oligodeoxynucleotide

<400> SEQUENCE: 23
ccgatgtaca ccaatgtgga ccaggacctc gtcggctggc gagcgccccc cggggcgcgt      60
tcc                                                                    63

<210> SEQ ID NO 24
<211> LENGTH: 80
<212> TYPE: DNA
<213> ORGANISM: Artificial Sequence
<220> FEATURE:
<223> OTHER INFORMATION: Description of Artificial Sequence: Synthetic
      oligodeoxynucleotide -continued

<400> SEQUENCE: 24
ccgcgtgcac ccgaggggtt gcgaaggcgg tggactttgt acccgtcgag tctatgggaa    60
ccactatgcg gtccccggtc                                                80

<210> SEQ ID NO 25
<211> LENGTH: 51
<212> TYPE: DNA
<213> ORGANISM: Artificial Sequence
<220> FEATURE:
<223> OTHER INFORMATION: Description of Artificial Sequence: Synthetic
      oligodeoxynucleotide

<400> SEQUENCE: 25
ccacgctaag cgtaggctgg ccaggggagc acccccctcc ttggccagct c              51

<210> SEQ ID NO 26
<211> LENGTH: 51
<212> TYPE: DNA
<213> ORGANISM: Artificial Sequence
<220> FEATURE:
<223> OTHER INFORMATION: Description of Artificial Sequence: Synthetic
      oligodeoxynucleotide

<400> SEQUENCE: 26
ccacgctaag cgtaggctgg ccaggggaga tcccccctcc ttggccagct c              51

<210> SEQ ID NO 27
<211> LENGTH: 3010
<212> TYPE: PRT
<213> ORGANISM: Hepatitis C virus

<400> SEQUENCE: 27

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Gln Pro Glu Gly Arg Ala Trp Ala Gln Pro Gly
65                  70                  75                  80

Tyr Pro Trp Pro Leu Tyr Gly Asn Glu Gly Leu Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Ile Pro Ala Ser Ala Tyr
            180                 185                 190

Glu Val Arg Asn Val Ser Gly Val Tyr His Val Thr Asn Asp Cys Ser
        195                 200                 205

-continued

Asn Ala Ser Ile Val Tyr Glu Ala Ala Asp Met Ile Met His Thr Pro
    210                 215                 220

Gly Cys Val Pro Cys Val Arg Glu Asn Asn Ser Ser Arg Cys Trp Val
225                 230                 235                 240

Ala Leu Thr Pro Thr Leu Ala Ala Arg Asn Ala Ser Val Pro Thr Thr
                245                 250                 255

Thr Ile Arg Arg His Val Asp Leu Leu Val Gly Ala Ala Ala Leu Cys
            260                 265                 270

Ser Ala Met Tyr Val Gly Asp Leu Cys Gly Ser Val Phe Leu Val Ala
        275                 280                 285

Gln Leu Phe Thr Phe Ser Pro Arg Arg His Glu Thr Val Gln Asp Cys
    290                 295                 300

Asn Cys Ser Ile Tyr Pro Gly His Val Thr Gly His Arg Met Ala Trp
305                 310                 315                 320

Asp Met Met Met Asn Trp Ser Pro Thr Ala Ala Leu Val Val Ser Gln
                325                 330                 335

Leu Leu Arg Ile Pro Gln Ala Val Val Asp Met Val Ala Gly Ala His
            340                 345                 350

Trp Gly Val Leu Ala Gly Leu Ala Tyr Tyr Ser Met Val Gly Asn Trp
        355                 360                 365

Ala Lys Val Leu Ile Val Met Leu Leu Phe Ala Gly Val Asp Gly Gly
    370                 375                 380

Thr Tyr Val Thr Gly Gly Thr Met Ala Lys Asn Thr Leu Gly Ile Thr
385                 390                 395                 400

Ser Leu Phe Ser Pro Gly Ser Ser Gln Lys Ile Gln Leu Val Asn Thr
                405                 410                 415

Asn Gly Ser Trp His Ile Asn Arg Thr Ala Leu Asn Cys Asn Asp Ser
            420                 425                 430

Leu Asn Thr Gly Phe Leu Ala Ala Leu Phe Tyr Val His Lys Phe Asn
        435                 440                 445

Ser Ser Gly Cys Pro Glu Arg Met Ala Ser Cys Ser Pro Ile Asp Ala
    450                 455                 460

Phe Ala Gln Gly Trp Gly Pro Ile Thr Tyr Asn Glu Ser His Ser Ser
465                 470                 475                 480

Asp Gln Arg Pro Tyr Cys Trp His Tyr Ala Pro Arg Pro Cys Gly Ile
                485                 490                 495

Val Pro Ala Ala Gln Val Cys Gly Pro Val Tyr Cys Phe Thr Pro Ser
            500                 505                 510

Pro Val Val Gly Thr Thr Asp Arg Phe Gly Val Pro Thr Tyr Ser
        515                 520                 525

Trp Gly Glu Asn Glu Thr Asp Val Leu Leu Leu Asn Asn Thr Arg Pro
    530                 535                 540

Pro Gln Gly Asn Trp Phe Gly Cys Thr Trp Met Asn Ser Thr Gly Phe
545                 550                 555                 560

Thr Lys Thr Cys Gly Gly Pro Pro Cys Asn Ile Gly Gly Ile Gly Asn
                565                 570                 575

Lys Thr Leu Thr Cys Pro Thr Asp Cys Phe Arg Lys His Pro Glu Ala
            580                 585                 590

Thr Tyr Thr Lys Cys Gly Ser Gly Pro Trp Leu Thr Pro Arg Cys Leu
        595                 600                 605

Val His Tyr Pro Tyr Arg Leu Trp His Tyr Pro Cys Thr Val Asn Phe
610                 615                 620

-continued

```
Thr Ile Phe Lys Val Arg Met Tyr Val Gly Gly Val Glu His Arg Leu
625                 630                 635                 640

Glu Ala Ala Cys Asn Trp Thr Arg Gly Glu Arg Cys Asn Leu Glu Asp
                645                 650                 655

Arg Asp Arg Ser Glu Leu Ser Pro Leu Leu Ser Thr Thr Glu Trp
            660                 665                 670

Gln Val Leu Pro Cys Ser Phe Thr Thr Leu Pro Ala Leu Ser Thr Gly
                675                 680                 685

Leu Ile His Leu His Gln Asn Val Val Asp Val Gln Tyr Leu Tyr Gly
            690                 695                 700

Ile Gly Ser Ala Val Val Ser Phe Ala Ile Lys Trp Glu Tyr Val Leu
705                 710                 715                 720

Leu Leu Phe Leu Leu Ala Asp Ala Arg Val Cys Ala Cys Leu Trp
                725                 730                 735

Met Met Leu Leu Ile Ala Gln Ala Glu Ala Leu Glu Asn Leu Val
                740                 745                 750

Val Leu Asn Ala Ala Ser Val Ala Gly Ala His Gly Ile Leu Ser Phe
            755                 760                 765

Leu Val Phe Phe Cys Ala Ala Trp Tyr Ile Lys Gly Arg Leu Val Pro
            770                 775                 780

Gly Ala Ala Tyr Ala Leu Tyr Gly Val Trp Pro Leu Leu Leu Leu
785                 790                 795                 800

Leu Ala Leu Pro Pro Arg Ala Tyr Ala Met Asp Arg Glu Met Ala Ala
                805                 810                 815

Ser Cys Gly Gly Ala Val Phe Val Gly Leu Ile Leu Thr Leu Ser
                820                 825                 830

Pro His Tyr Lys Leu Phe Leu Ala Arg Leu Ile Trp Trp Leu Gln Tyr
            835                 840                 845

Phe Ile Thr Arg Ala Glu Ala His Leu Gln Val Trp Ile Pro Pro Leu
850                 855                 860

Asn Val Arg Gly Gly Arg Asp Ala Val Ile Leu Leu Thr Cys Ala Ile
865                 870                 875                 880

His Pro Glu Leu Ile Phe Thr Ile Thr Lys Ile Leu Leu Ala Ile Leu
                885                 890                 895

Gly Pro Leu Met Val Leu Gln Ala Gly Ile Thr Lys Val Pro Tyr Phe
                900                 905                 910

Val Arg Ala His Gly Leu Ile Arg Ala Cys Met Leu Val Arg Lys Val
            915                 920                 925

Ala Gly Gly His Tyr Val Gln Met Ala Leu Met Lys Leu Ala Ala Leu
930                 935                 940

Thr Gly Thr Tyr Val Tyr Asp His Leu Thr Pro Leu Arg Asp Trp Ala
945                 950                 955                 960

His Ala Gly Leu Arg Asp Leu Ala Val Ala Val Glu Pro Val Phe
            965                 970                 975

Ser Asp Met Glu Thr Lys Val Ile Thr Trp Gly Ala Asp Thr Ala Ala
                980                 985                 990

Cys Gly Asp Ile Ile Leu Gly Leu Pro Val Ser Ala Arg Arg Gly Arg
                995                 1000                1005

Glu Ile His Leu Gly Pro Ala Asp Ser Leu Glu Gly Gln Gly Trp
            1010                1015                1020

Arg Leu Leu Ala Pro Ile Thr Ala Tyr Ser Gln Gln Thr Arg Gly
            1025                1030                1035

Leu Leu Gly Cys Ile Ile Thr Ser Leu Thr Gly Arg Asp Arg Asn
```

-continued

```
            1040                1045                1050
Gln Val Glu Gly Glu Val Gln Val Val Ser Thr Ala Thr Gln Ser
    1055                1060                1065
Phe Leu Ala Thr Cys Val Asn Gly Val Cys Trp Thr Val Tyr His
    1070                1075                1080
Gly Ala Gly Ser Lys Thr Leu Ala Gly Pro Lys Gly Pro Ile Thr
    1085                1090                1095
Gln Met Tyr Thr Asn Val Asp Gln Asp Leu Val Gly Trp Gln Ala
    1100                1105                1110
Pro Pro Gly Ala Arg Ser Leu Thr Pro Cys Thr Cys Gly Ser Ser
    1115                1120                1125
Asp Leu Tyr Leu Val Thr Arg His Ala Asp Val Ile Pro Val Arg
    1130                1135                1140
Arg Arg Gly Asp Ser Arg Gly Ser Leu Leu Ser Pro Arg Pro Val
    1145                1150                1155
Ser Tyr Leu Lys Gly Ser Ser Gly Gly Pro Leu Leu Cys Pro Ser
    1160                1165                1170
Gly His Ala Val Gly Ile Phe Arg Ala Ala Val Cys Thr Arg Gly
    1175                1180                1185
Val Ala Lys Ala Val Asp Phe Val Pro Val Glu Ser Met Glu Thr
    1190                1195                1200
Thr Met Arg Ser Pro Val Phe Thr Asp Asn Ser Ser Pro Pro Ala
    1205                1210                1215
Val Pro Gln Thr Phe Gln Val Ala His Leu His Ala Pro Thr Gly
    1220                1225                1230
Ser Gly Lys Ser Thr Lys Val Pro Ala Ala Tyr Ala Ala Gln Gly
    1235                1240                1245
Tyr Lys Val Leu Val Leu Asn Pro Ser Val Ala Ala Thr Leu Gly
    1250                1255                1260
Phe Gly Ala Tyr Met Ser Lys Ala His Gly Ile Asp Pro Asn Ile
    1265                1270                1275
Arg Thr Gly Val Arg Thr Ile Thr Thr Gly Ala Pro Ile Thr Tyr
    1280                1285                1290
Ser Thr Tyr Gly Lys Phe Leu Ala Asp Gly Gly Cys Ser Gly Gly
    1295                1300                1305
Ala Tyr Asp Ile Ile Ile Cys Asp Glu Cys His Ser Thr Asp Ser
    1310                1315                1320
Thr Thr Ile Leu Gly Ile Gly Thr Val Leu Asp Gln Ala Glu Thr
    1325                1330                1335
Ala Gly Ala Arg Leu Val Val Leu Ala Thr Ala Thr Pro Pro Gly
    1340                1345                1350
Ser Val Thr Val Pro His Pro Asn Ile Glu Glu Val Ala Leu Ser
    1355                1360                1365
Ser Thr Gly Glu Ile Pro Phe Tyr Gly Lys Ala Ile Pro Ile Glu
    1370                1375                1380
Thr Ile Lys Gly Gly Arg His Leu Ile Phe Cys His Ser Lys Lys
    1385                1390                1395
Lys Cys Asp Glu Leu Ala Ala Lys Leu Ser Gly Leu Gly Leu Asn
    1400                1405                1410
Ala Val Ala Tyr Tyr Arg Gly Leu Asp Val Ser Val Ile Pro Thr
    1415                1420                1425
Ser Gly Asp Val Ile Val Val Ala Thr Asp Ala Leu Met Thr Gly
    1430                1435                1440
```

-continued

```
Phe Thr Gly Asp Phe Asp Ser Val Ile Asp Cys Asn Thr Cys Val
    1445            1450                1455

Thr Gln Thr Val Asp Phe Ser Leu Asp Pro Thr Phe Thr Ile Glu
    1460            1465                1470

Thr Thr Thr Val Pro Gln Asp Ala Val Ser Arg Ser Gln Arg Arg
    1475            1480                1485

Gly Arg Thr Gly Arg Gly Arg Met Gly Ile Tyr Arg Phe Val Thr
    1490            1495                1500

Pro Gly Glu Arg Pro Ser Gly Met Phe Asp Ser Val Leu Cys
    1505            1510                1515

Glu Cys Tyr Asp Ala Gly Cys Ala Trp Tyr Glu Leu Thr Pro Ala
    1520            1525                1530

Glu Thr Ser Val Arg Leu Arg Ala Tyr Leu Asn Thr Pro Gly Leu
    1535            1540                1545

Pro Val Cys Gln Asp His Leu Glu Phe Trp Glu Ser Val Phe Thr
    1550            1555                1560

Gly Leu Thr His Ile Asp Ala His Phe Leu Ser Gln Thr Lys Gln
    1565            1570                1575

Ala Gly Asp Asn Phe Pro Tyr Leu Val Ala Tyr Gln Ala Thr Val
    1580            1585                1590

Cys Ala Arg Ala Gln Ala Pro Pro Pro Ser Trp Asp Gln Met Trp
    1595            1600                1605

Lys Cys Leu Ile Arg Leu Lys Pro Thr Leu His Gly Pro Thr Pro
    1610            1615                1620

Leu Leu Tyr Arg Leu Gly Ala Val Gln Asn Glu Val Thr Thr Thr
    1625            1630                1635

His Pro Ile Thr Lys Tyr Ile Met Ala Cys Met Ser Ala Asp Leu
    1640            1645                1650

Glu Val Val Thr Ser Thr Trp Val Leu Val Gly Gly Val Leu Ala
    1655            1660                1665

Ala Leu Ala Ala Tyr Cys Leu Thr Thr Gly Ser Val Val Ile Val
    1670            1675                1680

Gly Arg Ile Ile Leu Ser Gly Lys Pro Ala Ile Ile Pro Asp Arg
    1685            1690                1695

Glu Val Leu Tyr Arg Glu Phe Asp Glu Met Glu Glu Cys Ala Ser
    1700            1705                1710

His Leu Pro Tyr Ile Glu Gln Gly Met Gln Leu Ala Glu Gln Phe
    1715            1720                1725

Lys Gln Lys Ala Ile Gly Leu Leu Gln Thr Ala Thr Lys Gln Ala
    1730            1735                1740

Glu Ala Ala Ala Pro Val Val Glu Ser Lys Trp Arg Thr Leu Glu
    1745            1750                1755

Ala Phe Trp Ala Lys His Met Trp Asn Phe Ile Ser Gly Ile Gln
    1760            1765                1770

Tyr Leu Ala Gly Leu Ser Thr Leu Pro Gly Asn Pro Ala Ile Ala
    1775            1780                1785

Ser Leu Met Ala Phe Thr Ala Ser Ile Thr Ser Pro Leu Thr Thr
    1790            1795                1800

Gln His Thr Leu Leu Phe Asn Ile Leu Gly Gly Trp Val Ala Ala
    1805            1810                1815

Gln Leu Ala Pro Pro Ser Ala Ala Ser Ala Phe Val Gly Ala Gly
    1820            1825                1830
```

-continued

```
Ile Ala Gly Ala Ala Val Gly Ser Ile Gly Leu Gly Lys Val Leu
1835                1840                1845

Val Asp Ile Leu Ala Gly Tyr Gly Ala Gly Val Ala Gly Ala Leu
1850                1855                1860

Val Ala Phe Lys Val Met Ser Gly Glu Met Pro Ser Thr Glu Asp
1865                1870                1875

Leu Val Asn Leu Leu Pro Ala Ile Leu Ser Pro Gly Ala Leu Val
1880                1885                1890

Val Gly Val Val Cys Ala Ala Ile Leu Arg Arg His Val Gly Pro
1895                1900                1905

Gly Glu Gly Ala Val Gln Trp Met Asn Arg Leu Ile Ala Phe Ala
1910                1915                1920

Ser Arg Gly Asn His Val Ser Pro Thr His Tyr Val Pro Glu Ser
1925                1930                1935

Asp Ala Ala Ala Arg Val Thr Gln Ile Leu Ser Ser Leu Thr Ile
1940                1945                1950

Thr Gln Leu Leu Lys Arg Leu His Gln Trp Ile Asn Glu Asp Cys
1955                1960                1965

Ser Thr Pro Cys Ser Gly Ser Trp Leu Arg Asp Val Trp Asp Trp
1970                1975                1980

Ile Cys Thr Val Leu Thr Asp Phe Lys Thr Trp Leu Gln Ser Lys
1985                1990                1995

Leu Leu Pro Arg Leu Pro Gly Val Pro Phe Phe Ser Cys Gln Arg
2000                2005                2010

Gly Tyr Lys Gly Val Trp Arg Gly Asp Gly Ile Met Gln Thr Thr
2015                2020                2025

Cys Pro Cys Gly Ala Gln Ile Thr Gly His Val Lys Asn Gly Ser
2030                2035                2040

Met Arg Ile Val Gly Pro Arg Thr Cys Ser Asn Thr Trp His Gly
2045                2050                2055

Thr Phe Pro Ile Asn Ala Tyr Thr Thr Gly Pro Cys Thr Pro Ser
2060                2065                2070

Pro Ala Pro Asn Tyr Ser Arg Ala Leu Trp Arg Val Ala Ala Glu
2075                2080                2085

Glu Tyr Val Glu Val Thr Arg Val Gly Asp Phe His Tyr Val Thr
2090                2095                2100

Gly Met Thr Thr Asp Asn Val Lys Cys Pro Cys Gln Val Pro Ala
2105                2110                2115

Pro Glu Phe Phe Thr Glu Val Asp Gly Val Arg Leu His Arg Tyr
2120                2125                2130

Ala Pro Ala Cys Lys Pro Leu Leu Arg Glu Glu Val Thr Phe Leu
2135                2140                2145

Val Gly Leu Asn Gln Tyr Leu Val Gly Ser Gln Leu Pro Cys Glu
2150                2155                2160

Pro Glu Pro Asp Val Ala Val Leu Thr Ser Met Leu Thr Asp Pro
2165                2170                2175

Ser His Ile Thr Ala Glu Thr Ala Lys Arg Arg Leu Ala Arg Gly
2180                2185                2190

Ser Pro Pro Ser Leu Ala Ser Ser Ser Ala Ser Gln Leu Ser Ala
2195                2200                2205

Pro Ser Leu Lys Ala Thr Cys Thr Thr Arg His Asp Ser Pro Asp
2210                2215                2220

Ala Asp Leu Ile Glu Ala Asn Leu Leu Trp Arg Gln Glu Met Gly
```

```
                  2225                2230                2235
Gly Asn Ile Thr Arg Val Glu Ser Glu Asn Lys Val Val Ile Leu
            2240                2245                2250

Asp Ser Phe Glu Pro Leu Gln Ala Glu Asp Glu Arg Glu Val
    2255                2260                2265

Ser Val Pro Ala Glu Ile Leu Arg Arg Ser Arg Lys Phe Pro Arg
            2270                2275                2280

Ala Met Pro Ile Trp Ala Arg Pro Asp Tyr Asn Pro Pro Leu Leu
            2285                2290                2295

Glu Ser Trp Lys Asp Pro Asp Tyr Val Pro Pro Val His Gly
    2300                2305                2310

Cys Pro Leu Pro Pro Ala Lys Ala Pro Pro Ile Pro Pro Pro Arg
            2315                2320                2325

Arg Lys Arg Thr Val Val Leu Ser Glu Ser Thr Val Ser Ser Ala
            2330                2335                2340

Leu Ala Glu Leu Ala Thr Lys Thr Phe Gly Ser Ser Glu Ser Ser
            2345                2350                2355

Ala Val Asp Ser Gly Thr Ala Thr Ala Ser Pro Asp Gln Pro Ser
            2360                2365                2370

Asp Asp Gly Asp Ala Gly Ser Asp Val Glu Ser Tyr Ser Ser Met
            2375                2380                2385

Pro Pro Leu Glu Gly Glu Pro Gly Asp Pro Asp Leu Ser Asp Gly
            2390                2395                2400

Ser Trp Ser Thr Val Ser Glu Glu Ala Ser Glu Asp Val Val Cys
            2405                2410                2415

Cys Ser Met Ser Tyr Thr Trp Thr Gly Ala Leu Ile Thr Pro Cys
            2420                2425                2430

Ala Ala Glu Glu Thr Lys Leu Pro Ile Asn Ala Leu Ser Asn Ser
            2435                2440                2445

Leu Leu Arg His His Asn Leu Val Tyr Ala Thr Thr Ser Arg Ser
            2450                2455                2460

Ala Ser Leu Arg Gln Lys Lys Val Thr Phe Asp Arg Leu Gln Val
            2465                2470                2475

Leu Asp Asp His Tyr Arg Asp Val Leu Lys Glu Met Lys Ala Lys
            2480                2485                2490

Ala Ser Thr Val Lys Ala Lys Leu Leu Ser Val Glu Glu Ala Cys
            2495                2500                2505

Lys Leu Thr Pro Pro His Ser Ala Arg Ser Lys Phe Gly Tyr Gly
            2510                2515                2520

Ala Lys Asp Val Arg Asn Leu Ser Ser Lys Ala Val Asn His Ile
            2525                2530                2535

Arg Ser Val Trp Lys Asp Leu Leu Glu Asp Thr Glu Thr Pro Ile
            2540                2545                2550

Asp Thr Thr Ile Met Ala Lys Asn Glu Val Phe Cys Val Gln Pro
            2555                2560                2565

Glu Lys Gly Gly Arg Lys Pro Ala Arg Leu Ile Val Phe Pro Asp
            2570                2575                2580

Leu Gly Val Arg Val Cys Glu Lys Met Ala Leu Tyr Asp Val Val
            2585                2590                2595

Ser Thr Leu Pro Gln Ala Val Met Gly Ser Ser Tyr Gly Phe Gln
            2600                2605                2610

Tyr Ser Pro Gly Gln Arg Val Glu Phe Leu Val Asn Ala Trp Lys
            2615                2620                2625
```

-continued

```
Ala Lys Lys Cys Pro Met Gly Phe Ala Tyr Asp Thr Arg Cys Phe
    2630                2635                2640
Asp Ser Thr Val Thr Glu Asn Asp Ile Arg Val Glu Glu Ser Ile
    2645                2650                2655
Tyr Gln Cys Cys Asp Leu Ala Pro Glu Ala Arg Gln Ala Ile Arg
    2660                2665                2670
Ser Leu Thr Glu Arg Leu Tyr Ile Gly Gly Pro Leu Thr Asn Ser
    2675                2680                2685
Lys Gly Gln Asn Cys Gly Tyr Arg Arg Cys Arg Ala Ser Gly Val
    2690                2695                2700
Leu Thr Thr Ser Cys Gly Asn Thr Leu Thr Cys Tyr Leu Lys Ala
    2705                2710                2715
Ala Ala Ala Cys Arg Ala Ala Lys Leu Gln Asp Cys Thr Met Leu
    2720                2725                2730
Val Cys Gly Asp Asp Leu Val Val Ile Cys Glu Ser Ala Gly Thr
    2735                2740                2745
Gln Glu Asp Glu Ala Ser Leu Arg Ala Phe Thr Glu Ala Met Thr
    2750                2755                2760
Arg Tyr Ser Ala Pro Pro Gly Asp Pro Pro Lys Pro Glu Tyr Asp
    2765                2770                2775
Leu Glu Leu Ile Thr Ser Cys Ser Ser Asn Val Ser Val Ala His
    2780                2785                2790
Asp Ala Ser Gly Lys Arg Val Tyr Tyr Leu Thr Arg Asp Pro Thr
    2795                2800                2805
Thr Pro Leu Ala Arg Ala Ala Trp Glu Thr Ala Arg His Thr Pro
    2810                2815                2820
Val Asn Ser Trp Leu Gly Asn Ile Ile Met Tyr Ala Pro Thr Leu
    2825                2830                2835
Trp Ala Arg Met Ile Leu Met Thr His Phe Phe Ser Ile Leu Leu
    2840                2845                2850
Ala Gln Glu Gln Leu Glu Lys Ala Leu Asp Cys Gln Ile Tyr Gly
    2855                2860                2865
Ala Cys Tyr Ser Ile Glu Pro Leu Asp Leu Pro Gln Ile Ile Gln
    2870                2875                2880
Arg Leu His Gly Leu Ser Ala Phe Ser Leu His Ser Tyr Ser Pro
    2885                2890                2895
Gly Glu Ile Asn Arg Val Ala Ser Cys Leu Arg Lys Leu Gly Val
    2900                2905                2910
Pro Pro Leu Arg Val Trp Arg His Arg Ala Arg Ser Val Arg Ala
    2915                2920                2925
Arg Leu Leu Ser Gln Gly Gly Arg Ala Ala Thr Cys Gly Lys Tyr
    2930                2935                2940
Leu Phe Asn Trp Ala Val Arg Thr Lys Leu Lys Leu Thr Pro Ile
    2945                2950                2955
Pro Ala Ala Ser Gln Leu Asp Leu Ser Ser Trp Phe Val Ala Gly
    2960                2965                2970
Tyr Ser Gly Gly Asp Ile Tyr His Ser Leu Ser Arg Ala Arg Pro
    2975                2980                2985
Arg Trp Phe Met Trp Cys Leu Leu Leu Leu Ser Val Gly Val Gly
    2990                2995                3000
Ile Tyr Leu Leu Pro Asn Arg
    3005                3010
```